(12) United States Patent
Imai et al.

(10) Patent No.: US 7,452,988 B2
(45) Date of Patent: Nov. 18, 2008

(54) VECTOR FOR SUPPRESSION OF LACHRYMATORY FACTOR SYNTHASE (LFS) IN TRANSGENIC ONIONS

(75) Inventors: Shinsuke Imai, Higashi-Osaka (JP);
Nobuaki Tsuge, Higashi-Osaka (JP);
Tsunchiro Kamata, Higashi-Osaka (JP);
Noriya Masamura, Higashi-Osaka (JP);
Jinji Shono, Higashi-Osaka (JP);
Kentaro Horie, Fukaya (JP)

(73) Assignee: House Foods Corporation, Osaka (JP)

( * ) Notice: Subject to any disclaimer, the term of this patent is extended or adjusted under 35 U.S.C. 154(b) by 0 days.

(21) Appl. No.: 10/932,950

(22) Filed: Sep. 1, 2004

(65) Prior Publication Data

US 2005/0022263 A1    Jan. 27, 2005

Related U.S. Application Data

(63) Continuation of application No. PCT/JP03/02397, filed on Feb. 28, 2003.

(30) Foreign Application Priority Data

| Mar. 1, 2002 | (JP) | ............................. 2002-056523 |
| Mar. 1, 2002 | (JP) | ............................. 2002-056558 |
| Sep. 20, 2002 | (JP) | ............................. 2002-275799 |

(51) Int. Cl.
*C07H 21/04* (2006.01)
*C12N 15/82* (2006.01)
*A01H 5/00* (2006.01)

(52) U.S. Cl. .................... 536/24.5; 536/23.2; 536/23.6; 435/320.1; 435/468; 435/419; 800/286; 800/285; 800/298; 800/278

(58) Field of Classification Search ........................ None
See application file for complete search history.

(56) References Cited

U.S. PATENT DOCUMENTS 5,702,933 A * 12/1997 Klee et al. .................. 800/283

FOREIGN PATENT DOCUMENTS

| CA | 2 374 527 | 9/2003 |
| CA | 2 478 014 | 9/2003 |
| CA | 2374527 | 9/2003 |
| CA | 2478014 | 9/2003 |
| EP | 1 316 612 | 8/2001 |
| JP | 10-295373 | 11/1998 |
| WO | WO 02/20808 | 3/2002 |

OTHER PUBLICATIONS

Eady et al. Agrobacterium tumefaciens-mediated transformation and transgenic-plant regeneration of onion (Allium cepa L.). (2000) Plant Cell Reports, vol. 19, pp. 376-381.*
Elomaa P. et al. Transformation of antisense constructs of the chalcone synthase gene sperfamily into Gerbera hybrida: differential effect on the expression of family members. (1996) Molecular Breeding, vol. 2, pp. 41-50.*
Colliver et al. Differential modification of flavonoid and isoflavonoid biosynthesis with an antisense chalcone synthase construct in transgenic lotus comiculatus. (1997) PMB, vol. 35, pp. 509-522.*
Horesh et al. A rapid method for detection of putative RNAi target genes in genomic data. (2003) Bioinformatics; vol. 19, pp. ii73-ii80.*
Imai, S. et al., An onion enzyme that makes the eyes water., Nature 2002, vol. 419, p. 685.
English Abstract of JP 10-295373.
International Search Report completed May 27, 2003 for International Application No. PCT/JP03/02397.
International Preliminary Examination Report mailed Feb. 3, 2004, for International Application No. PCT/JP03/02397.
Written Opinion mailed Oct. 28, 2003, for International Application No. PCT/JP03/02397.
Yosida et al.; Purification, Properties, and N-Terminal Amino Acid Sequences of Guar Gum-degrading Enzyme from *Bacillus circulans* K-1; Biosci. Biotech Biochem., 61 (2), 251-255; 1997.
Wang et al.; An Isoelectric Separation of Soybean β-Amylase Isoforms and Their Enzymic Characteristics; Biosci. Biotechnol. Biochem., 63 (4), 726-730, 1999.
Di Ilio et al.; Glutathione transferase isoenzymes from *Bufo bufo* embryos at an early developmental stage; Biochem. J. (1992) 283, 217-222.

* cited by examiner

*Primary Examiner*—Anne Kubelik
*Assistant Examiner*—Cathy Kingdon Worley
(74) *Attorney, Agent, or Firm*—Hoffmann & Baron, LLP

(57) ABSTRACT

The present invention provides DNA and RNA designed on the basis of the sequence of an enzyme gene for repressing the expression of the enzyme gene generating a lachrymatory factor from a precursor of the lachrymatory factor, and also a vector for introducing DNA for repressing the expression of the gene of the lachrymatory factor-producing enzyme into a vegetable.

11 Claims, 5 Drawing Sheets

LFS ACTIVITY OF TRANSFORMED
RE-DIFFERENTIATED VEGETABLE

AMOUNT OF LFS PROTEIN IN TRANSFORMED RE-DIFFERENTIATED VEGETABLE

VECTOR FOR SUPPRESSION OF LACHRYMATORY FACTOR SYNTHASE (LFS) IN TRANSGENIC ONIONS

CROSS-REFERENCE TO RELATED APPLICATIONS

This application is a continuation of International Application No. PCT/JP03/02397, which designates the U.S., filed Feb. 28, 2003, which claims priority to Japanese Application No. 2002-56523, filed Mar. 1, 2002, Japanese Application No. 2002-56558, filed Mar. 1, 2002 and Japanese Application No. 2002-275799, filed Sep. 20, 2002, the contents of which are incorporated by reference herein.

TECHNICAL FIELD

The present invention relates to DNA and a vector for repressing expression of DNA (gene of lachrymatory factor-producing enzyme) encoding a protein or polypeptide having an effect of converting 1-propenylsulfenic acid into the lachrymatory factor, generated when plants such as onions are broken into pieces or cut. The present invention also relates to a method for repressing the expression of the gene of the lachrymatory factor-producing enzyme with them and vegetables having repressed expression of the gene of the lachrymatory factor-producing enzyme.

The term "lachrymatory factor" (hereinafter referred to as "LF") in this specification indicates thiopropanal-S-oxide. The expression "to have the lachrymatory factor-producing enzymatic activity" indicates to have an effect of converting trans-1-propenylsulfenic acid, which is an estimate substrate of the lachrymatory factor-producing enzyme, into a lachrymatory factor or an effect of generating the lachrymatory factor from trans-S-1-propenyl-cystein sulfoxide (PeCSO) contained in onions or the like in the presence of an enzyme named alliinase.

BACKGROUND ART

The most notable characteristic feature of onion is that a large amount of a lachrymatory factor (hereinafter referred to as "LP") is generated when it is pulverized or cut. Therefore, the generation of LF is a serious problem not only in cooking in ordinary kitchens but also in factories for producing dry onion. Under these conditions, various investigations were made on the chemical structure of LF and the generation process thereof. It was reported that LF is essentially thiopropanal S-oxide (Wilkins, W. F., ph. D. thesis, Cornell University, Ithaca, N.Y., 1961), that S-1-propenyl-cystein sulfoxide (hereinafter referred to as "PeCSO") which is a sulfur-containing compound contained in onion is decomposed by alliinase (Virtanen, A. I. et al. Suom. Kemistil. B, 34, 72, 1961) and that LF is generated through 1-propenylsulfenic acid which is a decomposition product of PeCSO with alliinase (Block, e. et al., J. Am. Chem. Soc., 11, 2200, 1979).

Because it was considered that LF is formed by the decomposition of PeCSO with alliinase in the prior art, there was proposed a method for producing onion generating a reduced amount of LF, which comprises the production of onion having a reduced PeCSO content or the production of onion having a reduced alliinase activity.

Under the circumstances, investigations were made for the purpose of varying the amount of PeCSO accumulated in onion by varying the cultivating conditions. For example, it was reported that when onion is cultivated under a low sulfur content condition, LF content is reduced (Randle, W. M. et al., J. Agr. Food Chem. 42, 2085, 1994) and the relative amount of PeCSO to the substrate of alliinase is also reduced (Randle, W. M. et al., J. Amer. Soc. Hort. Sci. 120, 1075, 1995). It was also reported that when onion is cultivated in the presence of selenium, the product has a reduced PeCSO content (Kopsell, D. E. et al., J. Amer. Soc Hort. Sci. 124, 307, 1999) and PeCSO content of the obtained onion is increased during the storage thereof (Kopsell, D. E. et al., J. Amer. Soc Hort. Sci. 124, 177, 1999) and that the larger the amount of ammonium nitrate used as a fertilizer, the lower PeCSO content (Randle, W. M. et al., J. Amer. Soc Hort. Sci. 125, 254, 2000).

However, the onion cultivated in the presence of a reduced amount of PeCSO has a problem that the smell is weakened (p. 41-52. In: S. J. Risch and C. Ho(eds.). Spices: Flavor chemistry and antioxidant properties. Amer. Chem. Soc., Wash., D.C.) and the relative amount of PeCSO to the substrate of alliinase is changed to change of the quality of the smell per se. Thus, only the change in the cultivation conditions is not a fundamental solution for the following reason: 1-Propenylsulfenic acid produced by the decomposition of PeCSO with alliinase is converted into not only LF but also thiosulfinate compounds which are the source of the smelling ingredients.

The applicant found a lachrymatory factor-producing enzyme capable of converting 1-propenylsulfenic acid into LF and applied it for patent (Japanese Patent Unexamined Published Application (hereinafter referred to as "J. P. KOKAI") No. Hei 10-295373). The applicant further elucidated an isozyme of this lachrymatory factor-producing enzyme, amino acid sequence thereof and DNA encoding the isozyme, and applied them for patent (International Patent Application PCT/JP01/07465).

Supposedly, if the expression of the lachrymatory factor-producing enzyme can be repressed and the activity thereof is inhibited by using the lachrymatory factor-producing enzyme elucidated in the above-described patent application, LF is not produced from 1-propenylsulfenic acid but the thiosulfinate compounds which give off the smell can be produced in an amount not less than that in the prior art irrespectively of the effect of the enzyme. In addition, according to genetic information of a gene encoding the lachrymatory factor-producing enzyme, the genetic recombination, induction of variation, and mating can be effectively conducted. Additionally, a technique of producing vegetables such as onion in which the lachrymatory factor is not easily formed by the pulverization or cutting thereof can be developed.

The main point of the present invention is to obtain vegetables having repressed expression of the lachrymatory factor-producing enzyme by a genetic engineering technique for efficiently producing intended vegetables in a short period according to the sequence information of the gene encoding the lachrymatory factor-producing enzyme of the prior application.

Namely, the object of the present invention is to provide DNA and RNA designed on the basis of the sequence of a gene of an enzyme for forming the lachrymatory factor from a precursor of this factor for the purpose of repressing the expression, and also a vector required for introducing the expression-repressing DNA of the gene of the lachrymatory factor-producing enzyme into a vegetable. Another object of the present invention is to provide a method for repressing the expression of the gene of the lachrymatory factor-producing enzyme by using them and also a vegetable in which the expression of the gene of the lachrymatory factor-producing enzyme is repressed. The present invention has great advantages that because the formation of the lachrymatory factor can be essentially repressed, the onion is not influenced by other external factors and also that because no influence is exerted on the amount of the precursor of the lachrymatory factor, the quality of onion is not lowered. Another advantage of the present invention is that the expression of the gene can be repressed in a period shorter than that in ordinary techniques of breeding vegetables which are free from the genetic engineering.

SUMMARY OF THE INVENTION

After intensive investigations made for the purpose of solving the above-described problems, the inventors have succeeded in constructing a means of repressing the expression of a gene of a lachrymatory factor-producing enzyme by using DNA encoding protein or polypeptide of the lachrymatory factor-producing enzyme having an effect of converting 1-propenylsulfenic acid into the lachrymatory factor.

The present invention also relates to DNA usable for repressing the expression of the gene of the lachrymatory factor-producing enzyme on the basis of the above-described sequence. The DNA constitution is as follows:

DNA comprising at least one sequence selected from the following sequences and a regulatory sequence connected to said sequence so as to make the transcription possible:

(a) a gene sequence of a lachrymatory factor-producing enzyme or a part of the gene sequence in a sense orientation, an antisense orientation or both the orientations;

(b) a regulatory sequence of the DNA in the vegetable genome DNA determined on the basis of the gene sequence of the lachrymatory factor-producing enzyme or a part of the regulatory sequence in a sense orientation, an antisense orientation or both the orientations; and (c) a DNA sequence located between the gene sequence of the lachrymatory factor-producing enzyme and the regulatory sequence of the DNA in the vegetable genome DNA determined on the basis of the gene sequence or a part of the DNA sequence in a sense orientation, an antisense orientation or both the orientations.

The term "gene of lachrymatory factor-producing enzyme" herein indicates a DNA region (structural gene) defining the primary structure of the lachrymatory factor-producing enzyme. The term "regulatory sequence in vegetable genome DNA determined on the basis of the gene of the lachrymatory factor-producing enzyme" generally indicates a DNA element on a gene comprising a core promoter of the gene of the lachrymatory factor-producing enzyme and a regulatory element (regulatory gene). DNA located between the gene of the lachrymatory factor-producing enzyme and a regulatory sequence in the vegetable genome DNA determined on the basis of this gene indicates a DNA region (intermediate sequence) between the above-described structural gene and the regulatory gene (refer to FIG. 1). The whole or a part of the DNA regions are transcribed into mRNA ("*Wakariyasui Idenshi Kogaku* edited by Hiroshi Handa, published by Shokodo in 1999). Thus, these gene regions are important for the production of the lachrymatory factor-producing enzyme. The expression "a part of the sequence" herein indicates a sequence having at least 18 nucleotides, preferably at least 22 nucleotides in any part in the above-described sequences (a), (b) and (c).

(2) DNA comprising a sequence producing one or more RNA having an endonuclease activity, at least one sequence selected from the following sequences and a regulatory sequence connected to said sequences so as to make the transcription possible:

(a) a gene sequence of a lachrymatory factor-producing enzyme or a part of the gene sequence in an antisense orientation;

(b) a regulatory sequence of a DNA in a vegetable genome DNA determined on the basis of the gene of the lachrymatory factor-producing enzyme or a part of the regulatory sequence in an antisense orientation; and (c) a DNA sequence located between the gene of the lachrymatory factor-producing enzyme and the regulatory sequence of DNA in the vegetable genome DNA determined on the basis of the gene or a part of the DNA sequence in an antisense orientation.

The present invention also relates to RNA having a base sequence capable of hybridizing with RNA corresponding to DNA comprising at least one sequence selected from the following sequences:

(a) a gene sequence of a lachrymatory factor-producing enzyme or a part of the gene sequence in a sense orientation, an antisense orientation or both the orientations;

(b) a regulatory sequence of a DNA in a vegetable genome DNA determined on the basis of the gene of the lachrymatory factor-producing enzyme or a part of the regulatory sequence in a sense orientation, an antisense orientation or both orientations; and (c) a DNA sequence located between the gene of the lachrymatory factor-producing enzyme and the regulatory sequence of the DNA in the vegetable genome DNA determined on the basis of the gene or a part of the DNA sequence in a sense orientation, an antisense orientation or both orientations.

The expression "RNA corresponding to DNA" herein indicates RNA having the same base sequence as that of DNA except that T (thymine) in DNA is replaced with U (uracil) in RNA. For example, when DNA having sequence (a) in the sense orientation is used, the corresponding RNA has a sequence in the sense orientation, and RNA hybridizable with this RNA has a sequence in the antisense orientation. Namely, RNA having the sequence in the antisense orientation corresponds to antisense RNA having a base sequence complementary to mRNA corresponding to DNA of sequence (a) in the sense orientation.

The present invention includes RNA excluding antisense RNA having a base sequence complementary to mRNA corresponding to DNA having a base sequence of SEQ ID NO. 11.

DISCLOSURE OF THE INVENTION (DNA of Vegetables)

The proteins capable of catalyzing the reaction for converting PeCSO, which is a precursor for the lachrymatory factor, into the lachrymatory factor include alliinase and lachrymatory factor-producing enzymes. They are contained in *allium* vegetables which produce the lachrymatory factors by a physical damage such as cutting, e.g. onion, green onion, shallot, leek, echarote and chive. The genes of the lachrymatory factor-producing enzyme include green onion DNA of SEQ ID NOS. 1 and 3, shallot DNA of SEQ ID NO. 5, echarote DNA of SEQ ID NO. 7, leek DNA of SEQ ID NOS. 9 and 13, onion DNA of SEQ ID NO. 11 and elephant garlic DNA of SEQ ID NO. 15. However, the genes of the lachrymatory factor-producing enzymes are not limited to them. In the above-described base sequences of DNA or a part of the sequence thereof, one or more bases may be added, deleted or replaced. For example, DNA or a part of the sequence thereof may encode the proteins or polypeptides wherein in the amino acid sequences of SEQ ID NOS. 2, 4, 6, 8, 10, 12, 14 and 16 corresponding to the above-described DNA, one or more amino acids may be added, deleted or replaced. Said proteins or polypeptides have a function of converting 1-propenylsulfenic acid into the lachrymatory factor.

The genes of the lachrymatory factor-producing enzyme are DNA or a part of the sequence thereof capable of hybridizing with DNA of a base sequence of the above-described SEQ ID NO. 1, 5, 7, 9, 13 or 15 under stringent conditions. The hybridizable DNA or a fraction thereof includes both DNA hybridizable with DNA of a base sequence of each SEQ ID number and complementary DNA. In other words, this DNA or a part of the sequence thereof consists of a base sequence having a homology of at least 60%, preferably at least 70% and more preferably at least 75% with the base sequence of the above-described SEQ ID NO. 1, 5, 7, 9, 13 or 15.

(Hybridization Conditions of Base Sequence)

The expression "stringent conditions" in the present invention herein indicates such conditions that base sequence of SEQ ID NO. 1, 5, 7, 9, 11, 13 or 15 or a part thereof is specifically hybridized with DNA and that nonspecific hybrid is not generated or detected. It is difficult to numerically express the stringent conditions. An example of the conditions is as follows: even when a hybrid is formed under such hybridization conditions that a hybridization buffer containing 30% (v/v) deionized formaldehyde, 0.6 M of NaCl, 0.04 M of $NaH_2PO_4$, 2.5 mM of EDTA and 7% of SDS is used at 42° C. and then the formed hybrid is washed with 2×SSC, 0.1% SDS, the hybrid is still kept. The hybridization of nucleic acids can be performed according to, for example, Molecular Cloning: A laboratory manual (1989) Cold Spring Harbor Laboratory Press, New York, USA.

(Homology in Base Sequence)

The homology in the base sequence is judged as follows: The alignment of the base sequence conducted prior to the judgment of the homology of bases in the sequences is conducted by using CLUSTAL W 1.81 DDBJ extended version (the algorism is conducted according to Gene 73, (1988) 237-244; CLUSTAL W by DDBJ) which is an internet analysis service of DNA Data Bank of Japan. The analysis parameter is kept default (gapdist: 8, maxdiv: 40, gapopen: 15, gapext: 6.66). The alignment results thus obtained are used for calculating the percentage of the number of the bases coincided in ORF based on the total number of the bases of ORF (gap region formed by the alignment is excluded) to calculate the homology of the bases in ORF.

(Method for Repressing Gene Expression)

The above-described DNA encodes protein of the lachrymatory factor-producing enzymes of the *allium* vegetables and, therefore, the generation of the lachrymatory factor can be repressed by controlling the expression of these DNA. For repressing the expression of the genes of the lachrymatory factor-producing enzymes, various methods well-known in the art can be employed in the present invention. The repression of the expression of genes includes the repression of the transfer of the genes and also the repression of the translation from mRNA to protein, and it also includes not only the complete termination of the expression of genes but also reduction of the expression.

Recently, various cases of the production of vegetables transformed by the improvement in the technique of culturing plant tissue and also in the technique of introducing genes were reported. As for *allium* vegetables, it was already reported that an extrinsic gene was introduced with *Agrobacterium* (C. C. Eady et al., Plant Cell Reports, 19, 376-381 (2000), S-J. Zheng et al., Molecular Breeding, 7, 101-115 (2001)) and that an extrinsic gene was introduced with a particle gun (C. C. Eady et al., Plant Cell Reports, 15, 958-962 (1996)). As the techniques of repressing the expression of a gene of a vegetable by the gene introduction technique, those described below have been known.

In one of the techniques, the function of RNA is repressed by an antisense RNA or, in other words, RNA having a base sequence complementary to mRNA which is an information of the protein synthesis. The antisense RNA can be artificially produced by a genetic recombination technique. For example, a petunia having a flower color different from that of a wild petunia producing antisense RNA of a chalcone synthase concerting the synthesis of the flower pigment was proposed (European Patent Publication No. 341885). Further, the expression of polygalacturonase gene having an important role for softening tomato fruits with antisense RNA was repressed to produce tomatoes which can be stored for a time longer than that of wild type tomatoes (European Patent Publication No. 891115).

In addition, a phenomenon called "co-suppression" was reported (C. Napoli et al., Plant Cell, 2, 279 (1990), and A. R. van der Krol et al., Plant Cell, 2, 291 (1990). In this phenomenon, when DNA constructed so as to produce sense RNA having a sequence homologous to that of an intrinsic gene is introduced, the expression of the introduced extrinsic gene and that of the intrinsic gene homologous thereto are repressed.

In addition to these two methods ("method for the introduction of antisense strand" and "method for the introduction of sense strand"), recently, a new method for repressing the expression of genes called "RNAi (RNA interference)" is known (J. Z. Levin et al., Plant Molecular Biology, 44, 759-775 (2000, Senri Ushida, "Protein, Nucleic acid, Enzyme" 46 (10), 1381-1386 (2001)). In this method, double strand RNA (dsRNA) homologous to a target gene is directly introduced into a cell by a technique of electroporation, microinjection, particle gun or the like, or a DNA sequence which expresses dsRNA is integrated. The fact that dsRNA is obtained by the complementary linking of sense RNA strand and antisense RNA strand indicates that the sense DNA strand and antisense DNA strand are introduced together. Irrespective of the method of the introduction (the introduction of the sense DNA strand and antisense DNA strand separately or the introduction of the combination of them), the final product obtained from the respective introduced genes is dsRNA complementary to the target gene. This product is decomposed into short dsRNA (siRNA) comprising twenty odd nucleotides with endonuclease. Further, when siRNA is linked to the complementary part of mRNA from the structural gene, the linked part becomes a guide for RNA processing complex (RISC) comprising two or more subunits and also the target mRNA is cut at the center of the guide RNA with RISC. Such a mechanism was proposed (V. Vance et al., Science, 292, 22 June 2277-2280 (2001)). Thus, it can be said that the above-described three methods have the same effect of repressing the gene expression after the transcription, although they are different from one another in the orientation and combination of the genes to be integrated.

The DNA of the present invention usable for repressing the expression of the gene of the lachrymatory factor-producing enzyme in the above-described methods is as follows:

DNA comprising at least one sequence selected from the following sequences and a regulatory sequence connected to said sequence so as to make the transcription possible:

(a) a gene sequence of a lachrymatory factor-producing enzyme in a sense orientation, an antisense orientation or both the orientations, or a part of the DNA sequence in a sense orientation, an antisense orientation or both the orientations;

(b) a regulatory sequence of a DNA in a vegetable genome DNA determined on the basis of the gene of the lachrymatory factor-producing enzyme in a sense orientation, an antisense orientation or both the orientations, or a part of the regulatory sequence in a sense orientation, an antisense orientation or both the orientations; and (c) a DNA sequence located between the gene of the lachrymatory factor-producing enzyme and the regulatory sequence of the DNA in the vegetable genome DNA determined on the basis of the gene in a sense orientation, an antisense orientation or both the orientations, or a part of the DNA sequence placed between them in a sense orientation, an antisense orientation or both the orientations.

The sense orientation and antisense orientation of the genes are shown in FIG. 1.

Any of the sequences (a), (b) and (c) can be used as the DNA for repressing the expression of the gene of the lachrymatory factor-producing enzyme of the present invention. Among them, a sequence of a part which can be transcribed as mRNA is preferred and, in particular, a part of (a) of the structural gene is preferred.

The sequence (a) used in the DNA for repressing the expression of the gene of the lachrymatory factor-producing enzyme may be the sequence of either the whole gene of the lachrymatory factor-producing enzyme or a part thereof. Further, it may be the sequence of the whole or a part of DNA encoding the above-described protein but in which one or more amino acids in the amino acid sequence of the protein are added, deleted or replaced.

The sequence (b) used in the DNA for repressing the expression of the gene of the lachrymatory factor-producing enzyme may be the whole regulatory sequence of DNA in vegetable genome DNA determined on the basis of the gene of the lachrymatory factor-producing enzyme or a sequence of a part thereof, or the whole or a part of the sequence obtained by the addition, deletion or replacement of one or more bases in the base sequence of the regulatory sequence.

The sequence (c) used in the DNA for repressing the expression of the gene of the lachrymatory factor-producing enzyme may be the sequence of the whole DNA located between the gene of the lachrymatory factor-producing enzyme and the regulatory sequence of the DNA in vegetable genome DNA determined on the basis of the gene, a sequence of a part thereof, or the whole or a part of the sequence obtained by the addition, deletion or replacement of one or more bases in the base sequence of the DNA sequence.

The present invention includes the regulatory sequence in the vegetable genome DNA and DNA located between the gene of the lachrymatory factor-producing enzyme and the regulatory sequence thereof (sequences (b) and (c)). These sequences can be determined on the basis of the base sequence of the gene of the lachrymatory factor-producing enzyme. Namely, the sequence is suitably cloned from the base sequence of the above-described gene. For example, the sequence can be screened from a genome library by using a proper part on 5' end side of cDNA having the complete length of the above-described sequence as a probe. In another method, a synthetic oligonucleotide for the N-terminal of the amino acid sequence is prepared and a gene fraction containing a promoter domain can be cloned from the genome library. It is also possible to clone the full length DNA without the preparation of the genome library by RACE method wherein an unknown domain is cloned from the above-described DNA by PCR.

RNA for repressing the expression of the gene of the lachrymatory factor-producing enzyme of the present invention indicates RNA transcribed from the above-described DNA for repressing the expression. Such RNA include artificially synthesized RNA having the same base sequences and directly usable for the repression.

The sequence in the sense or antisense nucleotides used in the present invention is preferably complementary to the whole or a part of the sequence of endogenous genes (or homologous genes) of a vegetable to be transformed. However, the complementation may be incomplete so far as the expression of the genes can be effectively repressed. For example, RNA transcribed from DNA having at least one of the DNA sequences of the present invention is preferably hybridized to form RNA transcribed from the genes of the lachrymatory factor-producing enzyme, regulatory sequence at upstream side thereof and RNA transcribed from the DNA sequence between them. This RNA may be of either single strand or double strand.

(Nucleic Acid Molecule Having a Function of Inhibiting the Translation of mRNA of Protein or Polypeptide of Lachrymatory Factor-Producing Enzyme)

It was proved by the investigations of the present inventors that the lachrymatory factor-producing enzyme is an indispensable factor for forming the lachrymatory factor (J. P. KOKAI No. Hei 10-295373). Therefore, it is self-evident that when the action of this enzyme is inhibited, the lachrymatory factor is not formed.

Various investigations were made for the purpose of repressing the formation of the lachrymatory factor. They include a cultivation method wherein the amount of sulfur-containing fertilizers is reduced for reducing the accumulation of S-1-propenyl-cysteine sulfoxide (PeCSO) which is a substrate for alliinase and a method for inactivating alliinase for attaining the purpose. However, they cannot solve the problems while the quality of the product is kept high.

Thus, the method for repressing the steps ranging from the transcription to the translation of the gene encoding the lachrymatory factor-producing enzyme is very useful for the production of *allium* vegetables having a high quality and a repressed lachrymatory effect. This method cannot be performed unless the gene sequence of the enzyme is elucidated.

Various methods known in the art can be employed for inhibiting the expression of the gene of the lachrymatory factor-producing enzyme. The repression of the expression of gene includes the repression of the transcription of genes and the repression of the translation thereof into protein. For effectively inhibiting the expression of the genes, it is effective to repress the translation of mRNA of the lachrymatory factor-producing enzyme contained in *allium* vegetables.

Well-known techniques of the repression for the above-described purpose include an antisense method wherein the full length or a part of mRNA of intrinsic lachrymatory factor-producing enzyme is hybridized to form double strand RNA so that genes can be introduced while the subsequent translation is repressed and also RNAi method wherein double strand RNA of all the sequences of the enzyme or a part thereof is formed to introduce the gene so as to decompose mRNA of the intrinsic lachrymatory factor-producing enzyme. Another effective method comprises utilizing a co-repression wherein a gene is introduced to over-express the full length or a part of the sense strand or an analogous sequence of the lachrymatory factor-producing enzyme so as to repress the expression of a gene homologous thereto.

Namely, all the nucleic acid molecules capable of eliminating the function of the intrinsic mRNA by the above-described mechanisms or the like are effective irrespective of the length thereof, number of strands (single strand or double strand) or the hybridization with the genes of the lachrymatory factor-producing enzyme. The length of the nucleic acid molecules is at least 18 nucleotides, preferably at least 22 nucleotides. To say repeatedly, reasons why the design or the performance of such nucleic acid molecules has become possible are that the gene sequence of the lachrymatory factor-producing enzyme was elucidated and the design or the performance of them has become possible on the basis of the sequence.

(Test of the Effect of Nucleic Acid Molecules Inhibiting the Translation of mRNA)

For examining whether a nucleic acid molecule inhibited the translation of mRNA of the intrinsic lachrymatory factor-producing enzyme or not, it is effective to determine the lachrymatory factor-producing enzymatic activity of a vegetable tissue into which genes were introduced so as to translate the nucleic acid molecules into RNA or to determine the quantity of protein in the enzyme so as to directly confirm the effect. The fact that the lachrymatory factor-producing enzymatic activity is reduced or the amount of the protein in the enzyme is reduced indicates that the translation of intrinsic mRNA is inhibited by the introduced nucleic acid molecules. The effectiveness of the introduced nucleic acid molecules can be judged from those results.

For example, the lachrymatory factor-producing enzymatic activity is determined by adding an extract of a vegetable tissue to be tested to the reaction system of alliinase extracted from garlic and free from this enzyme and PeCSO which is the substrate of alliinase, and determining the generated lachrymatory factor (LF) by HPLC or the like. More concretely, the fact whether a transformed vegetable has the lachrymatory factor-producing enzymatic activity or not can be confirmed by a method described in International Patent Application PCT/JP01/07465 as will be shown in examples given below.

The fact that the amount of the protein in the lachrymatory factor-producing enzyme is reduced can be judged by western blotting method wherein an antibody of this enzyme prepared by using this enzyme as the antigen is used. Namely, this judgment can be conducted by the ordinary western blotting method wherein a fraction extracted from a vegetable tissue to be tested is fractionated by SDS-PAGE (SDS-polyacrylamide electrophoresis) and, after the blotting with PVDF membrane, the protein is selectively detected with the lachrymatory factor-producing enzyme antibody. The standard protein of the lachrymatory factor-producing enzyme used herein can be prepared by extracting it from various *allium* vegetables and purifying the extract. It is also possible to use a recombinant lachrymatory factor-producing enzyme obtained by the expression from DNA sequence of the enzyme with *E. coli* or the like. The determination method of the enzymatic activity and also the determination method of the amount of the protein in the lachrymatory factor-producing enzyme are not limited to the ordinary methods described herein but any method can be employed.

As a method for the application of antisense RNA, there is mentioned a method wherein DNA encoding a ribozyme is used. The word "ribozyme" means an RNA molecule having a catalytic activity. Ribozymes have various activities. In particular, investigations were made on ribozymes as enzymes for cleaving RNA to make it possible to design ribozymes used for site-specifically cleaving RBA. Ribozymes include those comprising 400 or more nucleotides such as those of intron type in group I and M1RNA contained in RNaseP and they also include those having an active domain of about 40 nucleotides, which are called hammer head type and hair pin type (Makoto Koizumi and Eiko Otsuka, "Protein, Nucleic acids, Enzyme", 35, 2191, 1990).

For example, a ribozyme of hammer head type cleaves 3' side of C of a sequence of GUC in a target mRNA. It was suggested that also when the sequence in the target mRNA is not only GUC but also GUA or GUU, it is cleaved by the ribozyme of the hammer head type (M. Koizumi et al., FEBSLett. 228:225, 1988). It is possible to produce a restriction-enzymatic RNA-cleaving ribozyme capable of recognizing the sequence of GUC, GUU or GUA in a target RNA (M. Koizumi et al., FEBS Lett. 239:285, 1988, Makoto Koizumi and Eiko Otsuka, "Protein, Nucleic acids, Enzyme", 35, 2191, 1990 and M. Koizumi et al., Nucleic Acids Res. 17:7059, 1989). There was also reported a method which comprises introducing a DNA sequence which produces a ribozyme having an effect of specifically cleaving RNA strand in addition to a DNA sequence which produces antisense RNA complementary to mRNA of a target gene into a vegetable (A. O. Merlo et al., Plant Cell,10, 1603-1622 (1998)). RNA produced from the introduced gene has such a property that the antisense RNA part thereof is complementary linked with RNA from the target gene to cleave RNA from the target gene by the endonuclease activity of the ribozyme part thereof, whereby the expression of the target gene is repressed.

The lachrymatory factor-producing enzyme of the present invention contains many sites which can be the targets of the ribozyme.

Hair pin-type ribozyme is also useful for the purpose of the present invention. The hair pin-type ribozyme is found in, for example, a minus strand of satellite RNA of tobacco ring spot virus (J. M. Buzayan, Nature 323:349, 1986). It is suggested that also this ribozyme is designed so as to cause the target-specific RNA cleavage (Y. Kikuchi and N. Sasaki, Nucleic Acids Res. 19:6751, 1992, and Hiroshi Kikuchi, *Kagaku to Seibutsu* 30:112, 1992).

The ribozyme designed so as to cleave the target is ligated with a promoter such as 35S promoter of cauliflower mosaic virus and a transcription terminating sequence so that it is transcribed in the vegetable cells. In this case, if a superfluous sequence is added to 5' terminal or 3' terminal of the transcribed RNA, the activity of the ribozyme might be lost. In such a case, it is possible to arrange another cis-acting trimming ribozyme for the trimming on 5' side or 3' side of the ribozyme part to as to precisely cleave only the ribozyme part from the transcribed ribozyme-containing RNA (K. Taira et al., Protein Eng. 3:733, 1990, A. M. Dzianott and J. J. Bujarski, Proc. Natl. Acad. Sci. USA. 86:4823, 1989, C. A. Grosshans and R. T. Cech, Nucleic Acids Res. 19:3875, 1991, K. Taira et al., Nucleic Acids Res. 19:5125, 1991). It is also possible to improve the effect by arranging the constitutive units in tandem so that two or more sites in the target gene can be cleaved (N. Yuyama et al., Biochem. Biophys. Res. Commun. 186:1271, 1992). The expression of the target gene of the present invention can be repressed by specifically cleaving the transcription product of the gene with the ribozyme. The techniques of using the ribozyme are described in J. P. KOKAI No. 2001-238686.

DNA for repressing the expression of the gene of the lachrymatory factor-producing enzyme of the present invention comprises:

a sequence producing one or more RNA having an endonuclease activity, at least one sequence selected from the following sequences and a regulatory sequence connected to said sequences so as to make the transcripts possible:

(a) a gene sequence of a lachrymatory factor-producing enzyme or a part of the gene sequence in an antisense orientation;

(b) a regulatory sequence of a DNA in a vegetable genome DNA determined on the basis of the gene of the lachrymatory factor-producing enzyme or a part of the regulatory sequence in an antisense orientation; and (c) a DNA sequence located between the gene of the lachrymatory factor-producing enzyme and the regulatory sequence of the DNA in the vegetable genome DNA determined on the basis of the gene or a part of the DNA sequence in an antisense orientation.

The sequences (a) to (c) used for the DNA for repressing the expression of the gene of the lachrymatory factor-producing enzyme are as described above.

For repressing the generation of the lachrymatory factor in vegetables by using the expression-repressing DNA of the gene of the lachrymatory factor-producing enzyme in the present invention, this DNA is inserted into a suitable vector, the vector is introduced into a vegetable cell and the transformed vegetable cell thus obtained is regenerated. The vectors used are not limited so far as they satisfy the following conditions:

The inserted gene can integrated into vegetable genome DNA.

The vector has at least 3 cloning sites for inserting the DNA to be introduced.

Promoters linked for expressing the introduced gene are not limited so far as they are capable of ordinarily expressing genes in vegetable cells. Those promoters are, for example, 35S promoter of cauliflower mosaic virus, ubiquitin-1 promoter of maize and nopaline synthase promoter.

The vegetable organs and tissues into which the gene is to be introduced are not limited so far as they keep the re-differentiating effect on the vegetable bodies. A callus tissue having the re-differentiating effect is preferred. Any of cultured cells, protoplasts, other vegetable organs and tissues having the re-differentiating effect is usable.

Methods for introducing the gene include, for example, a method wherein a vegetable is infected with a microorganism of *Agrobacterium* having a vector plasmid having the gene introduced therein, a method wherein a vector having the gene introduced therein is introduced into a vegetable protoplast by the electroporation method, and a method wherein the vector is introduced into a vegetable cell by the particle gun method ("*Model Shokubutsu no Jikken Protocol* (Experiment protocol of model plants)" compiled under the supervision of Isao Shimamoto et al. p. 82-98 (1996)).

The method for repressing the expression of the gene of the lachrymatory factor-producing enzyme is described above mainly with reference to the techniques of the sense, antisense, RNAi and ribozyme. Any of these techniques may be employed. One of the methods comprises the direct recombination of a part of the structural gene in vegetable genome DNA. For example, a method which can be employed herein comprises the introduction of a chimera oligonucleotide wherein RNA and DNA are linked complementarily to each other to cause a complementary recombination of a part of the structural genes in the vegetable genome. By previously replacing one or two bases in the sequence of the chimera oligonucleotide to be introduced with other bases different from those in the structural gene, mRNA transcribed from the recombined structural gene has one or two replaced bases. The variety of the amino acids translated from mRNA can be changed by suitably selecting the bases to be replaced. By altering the amino acids in the active center having an important role for the physiological activity of protein (activity of enzyme protein), the expression of the structural gene can be repressed. In the vegetables, the recombination frequency is limited to as low as $1/1000$ to $1/10000$ and number of the bases to be recombined is limited to 1 or 2 (T. Zhu et al., Proc. Natl. Acad. Sci. USA, 96, 8768-8773 (1999)). However, this technique is utilizable for repressing the expression of the target gene. In addition to the above-described chimeric nucleotide methods, gene targeting techniques such as T-DNA tagging technique and transposon tagging technique wherein vegetable genome DNA is directly attacked are also utilizable.

For repressing the effect of lachrymatory factor-producing enzyme, it is possible to employ a method wherein an inhibitor is added or a method wherein the onion is forced to produce the inhibitor. The method wherein the expression of the lachrymatory factor-producing enzyme per se is repressed is preferred because the inhibitor possibly exerts an influence on enzymes other than the lachrymatory factor-producing enzyme. The methods for repressing the expression of the lachrymatory factor-producing enzyme include a method wherein an intended variant vegetable is obtained by the irradiation with γ-rays or by using a variation-inducing chemical such as EMS (ethylmethane sulfonates) and a method wherein the intended variant vegetable is obtained by the mating. However, when the variation of a vegetable is induced, the variation might occur not only in the repression of the expression of the lachrymatory factor-producing enzyme and, therefore, the subsequent selection of the intended product is required to elongate the period of the technique in general.

MODE FOR CARRYING OUT THE INVENTION

The methods for the introduction of DNA for repressing the expression of the genes of the lachrymatory factor-producing enzyme and the selection and confirmation of the vegetables of repressed expression in the present invention are roughly as described below.

Preparation of Vector

A vector is prepared by linking any of the sequence in the sense orientation of the sequence of the full length of the gene of the lachrymatory factor-producing enzyme or a part thereof (preferably at least 18 bp, more preferably at least 22 bp), the sequence in the antisense orientation thereof and the sequence containing the both orientations with a downstream of the regulatory region (promoter), linking a terminator with a downstream thereof and integrating the product into a plasmid. The following process can be conducted according to an ordinary gene cloning technique:

A plasmid obtained by subcloning the gene of the lachrymatory factor-producing enzyme is introduced into *E. coli* (such as XL1-Blue) and proliferated. PCR is carried out by using the plasmid as the template to amplify the full length or a part of the sequence of the gene of the lachrymatory factor-producing enzyme. The amplified sequence is connected with a promoter to obtain an intended orientation. A terminator is added thereto and this sequence is integrated into the plasmid.

As the promoter, for example, 35S promoter of cauliflower mosaic virus is usable. Other promoters are also usable so far as the expression is possible in the vegetable cells. As the terminator, for example, nopaline synthase terminator is usable.

Although ordinary plasmids such as pBI101 can be used as the plasmids for the integration of the genes, the plasmids are not limited thereto. When a plasmid having a suitable selection marker (a marker resistant to antibiotics such as hygromycin and kanamycin) is used for the integration of the gene, the selection of the transformant is facilitated.

The plasmid can be recombined with *Agrobacterium* by propagating the plasmid in *E. coli* (such as HB101) and triparentally mating this *E. coli* with *E. coli* having a helper plasmid (such as HB101 (pRK2013)) and *Agrobacterium* having helper Ti plasmid (such as pAL4404) (for example,

*Agrobacterium tumefaciens* LBA4404 is preferred but other *Agrobacteriurm* bacteria such as EHA105 and EHA101 are also usable). In addition to the triparental mating with *E. coli* having the helper plasmid, it is also possible to directly introduce the plasmid having the introduced gene sequence into *Agrobacterium* by the electroporation method.

Preparation of Vegetable Materials Such as Onion to be Used for the Recombination The vegetable materials are not limited so far as they have a re-differentiation faculty (faculty of regenerating the vegetable body). In *Allium* vegetables such as onion, a callus having the re-differentiation faculty derived from the body of the vegetable is preferably used. The organs of the *allium* vegetables such as onion, from which the callus is derived, are, for example, mature or premature embryos from seeds, germinated primary root from seeds, growth point of scaly leaf and basal plate of onion bulb.

The composition of the culture medium in which the callus is derived is preferably the composition of MS medium usually usable for the culture of vegetables, and culture media having other compositions are also usable. An indispensable component of the medium for deriving the callus is auxin which is a phytohormone. The concentration of auxin is preferably 1 to 100 µM. Auxins preferred for deriving the callus include 4-FPA (4-fluorophenoxyacetic acid), Picrolam (4-amino-3,5,6-trichloro-2-pyridinecarboxylic acid), 2,4-D (2,4-dichlorophenoxyacetic acid), etc. Other auxins are also usable.

The callus is cultured under conditions suitable for the culture. It is preferably cultured under irradiation with a fluorescent light of about 1000 to 3000 lux at 25° C. The derived callus can be maintained by the subculture. For using the callus keeping its re-differentiation faculty, it is preferred that the culture period for the derivation of the callus is shortened and that the number of times of the subculture is reduced. Concretely, period of the culture for the callus derivation is about 3 to 4 months and number of times of the subculture is 3 or below.

When onion or the like is used, the re-differentiation faculty of the callus significantly varies depending on the variety thereof. It is thus desirable to use a variety having a higher-differentiation faculty. Preferred varieties of onion are, for example, Sen-shyuu-chu-kodakaki, kurenai, momiji and tenju.

Infection of Callus with Gene Introduction Vector

The microbes of *Agrobacterium* having the gene introduction vector obtained in (1) were propagated and a callus is dipped in the microbe suspension. It is important in this step to add acetosyringone which is a compound required for the infection of monocotyledons with *Agrobacterium*. The concentration of acetosyringone is preferably 100 to 200 µM.

After the cocultivation of the microbes and the callus for at least 3 days, preferably about 4 to 6 days, *Agrobacterium* is removed with an antibiotic such as cefotaxime (claforan) or carbenicillin.

Selection of Transformant Individuals from the Infected Callus

The callus is cultured and grown on a antibiotic-containing medium for a marker resistant to antibiotics such as hygromycin and kanamycin previously put into the vector and then it is re-differentiated. The living ones are the individuals succeeded in the transformation. As the composition of the culture medium used for there-differentiation from the callus, the composition of MS medium usually used for the culture of vegetables can be used and culture media having other compositions are also usable. It is important to remove auxin from the re-differentiation medium.

Confirmation of Transformant Individuals

The introduction of the intended gene into the re-differentiation vegetable is confirmed by extracting DNA from the vegetable and examining it by southern hybridization method (Hiroki Nakayama et al., Bio-experiment Illustrated *Idenshi Kaisetu no Kiso*, pages 137-151 (1995)). To confirm whether the re-differentiated vegetable has the lachrymatory factor-producing enzymatic activity or not, a method of International Patent Application PCT/JP01/07465 described below is employed.

(Method for Determining Lachrymatory Factor-Producing Enzymatic Activity)

A crude enzyme suspension extracted from transformed individuals is diluted with a diluting buffer (50 mM potassium phosphate buffer, pH 6.5). 40 µl of garlic alliinase (50 units/ml) and 20 µg/l of PeCSO solution (20 mg/ml) are added to 10 µl of the diluted sample. After carrying out the reaction at room temperature for 3 minutes, 1 µl of the reaction mixture is applied to HPLC to determine the amount of the lachrymatory factor thus obtained. For the analysis, ODS column (4.6 φ×250 mm) (a product of Senshuu Kagaku Co.) or DOCOSIL column (4.6 φ×250 mm) (a product of Senshuu Kagaku Co.) is used. 30% (v/v) acidic MeOH is used for the mobile phase, the flow rate is 0.6 ml/min, the column temperature is 35° C., and the detection is at 254 nm.

REFERENTIAL EXAMPLE

In the vegetables having a repressed expression of the lachrymatory factor-producing enzyme, the lachrymatory factor is not produced from 1-propenylsulfenic acid but this compound acts as a source of the smell irrespective of the enzyme and, in addition, it is expected that thiosulfinate compounds having an antiasthmatic effect are produced in an amount equal to or larger than that obtained in the prior art. This fact is proved by the experiments described below.

(1) Preparation of Crude Garlic Alliinase Free of the Lachrymatory Factor-Producing Enzyme 110 ml of distilled water was added to 110 g of fresh garlic produced in China, and they were broken into pieces with a mixer and then centrifuged to remove an insoluble matter. Hydrochloric acid was added to the obtained supernatant under stirring to adjust pH of the supernatant to 4. The stirring was continued for additional 30 minutes and then the precipitate thus formed was recovered by the centrifugation. The precipitate was dissolved in 50 ml of 50 mM potassium phosphate buffer containing 10% glycerol and 20 µM pyridoxal phosphate and having pH 6.5 and then the alliinase activity was determined. The solution was further diluted with 50 mM potassium phosphate buffer having pH 6.5 to adjust the concentration thereof to 6 units/ml. The above-described process was carried out at a low temperature.

(2) Preparation of Crude Garlic Alliinase Containing the Lachrymatory Factor-Producing Enzyme 250 ml of 20 mM potassium phosphate buffer containing 2.5 mg/L of pyridoxal phosphate and having pH 7.5 was added to 250 g of Sapporo yellow onion and they were broken into pieces with a mixer and then filtered and centrifuged to remove an insoluble matter. Ammonium sulfate was added to the obtained supernatant under stirring to adjust the concentration of the supernatant to 65%. The stirring was continued for additional 1 hour and then the precipitate thus formed was recovered by the centrifugation. The precipitate was dissolved in 50 ml of 50 mM potassium phosphate buffer containing 10% of glycerol, 0.05% of mercaptoethanol and 5 mM of EDTA and having pH 7.5. After the dialysis with 50 mM potassium phosphate buffer containing 10% glycerol, 0.05% mercaptoethanol and 5 mM EDTA and having pH 7.5 for 3 hours, the obtained product was centrifuged to remove an insoluble matter and then alliinase activity thereof was determined. The product was diluted with 50 mM potassium phosphate buffer at pH 6.5 to adjust the concentration thereof to 6 units/ml. The above-described process was carried out at a low temperature.

(3) The Determination of Thiosulfinates by N-ethyl Maleimide Method

350 µl of potassium phosphate buffer having pH 6.5 was added to 50 µl of 5 mg/ml PeCSO solution. Then 600 µl of 6 units/ml crude onion alliinase or crude garlic alliinase was added to the obtained mixture and they were reacted at room temperature for 1 minute. Immediately after the reaction, 500 µl of diethyl ether was mixed into the reaction mixture. After the centrifugation, 100 µl of a sample was taken from the diethyl ether layer. 300 µl of 0.05 M solution of N-ethyl maleimide in 2-propanol, 300 µl of 0.25 M solution of potassium hydroxide in 2-propanol and 450 µl of ascorbic acid solution obtained by dissolving 1 g of ascorbic acid in 100 ml of distilled water were added to the sample, and they were mixed together. The thiosulfinates were determined on the basis of the coloring at 515 nm.

The determination was conducted five times for the lachrymatory factor-containing crude alliinase from onion and also for the lachrymatory factor-free crude alliinase from garlic. The blank for each enzyme used in the tests was prepared by adding 50 µl of a potassium phosphate buffer having pH 6.5 in place of 50 µl of PeCSO solution.

(4) Results of the Determination

The results of the determination of the thiosulfinates are show in FIG. 2. It is understood from FIG. 2 that the amount of the thiosulfinates is more significantly increased by resolving PeCSO with the lachrymatory factor-free crude garlic alliinase than by resolving PeCSO with the lachrymatory factor-containing crude onion alliinase (t assay significance level: 1%). For the blanc of each enzyme, there was no significant difference even when the significance level was 5%. Thus, it can be expected that the amount of thiosulfinates formed can be increased by repressing the lachrymatory factor-producing enzyme in onion.

BEST MODE FOR CARRYING OUT THE INVENTION

EXAMPLES

Figure 1:
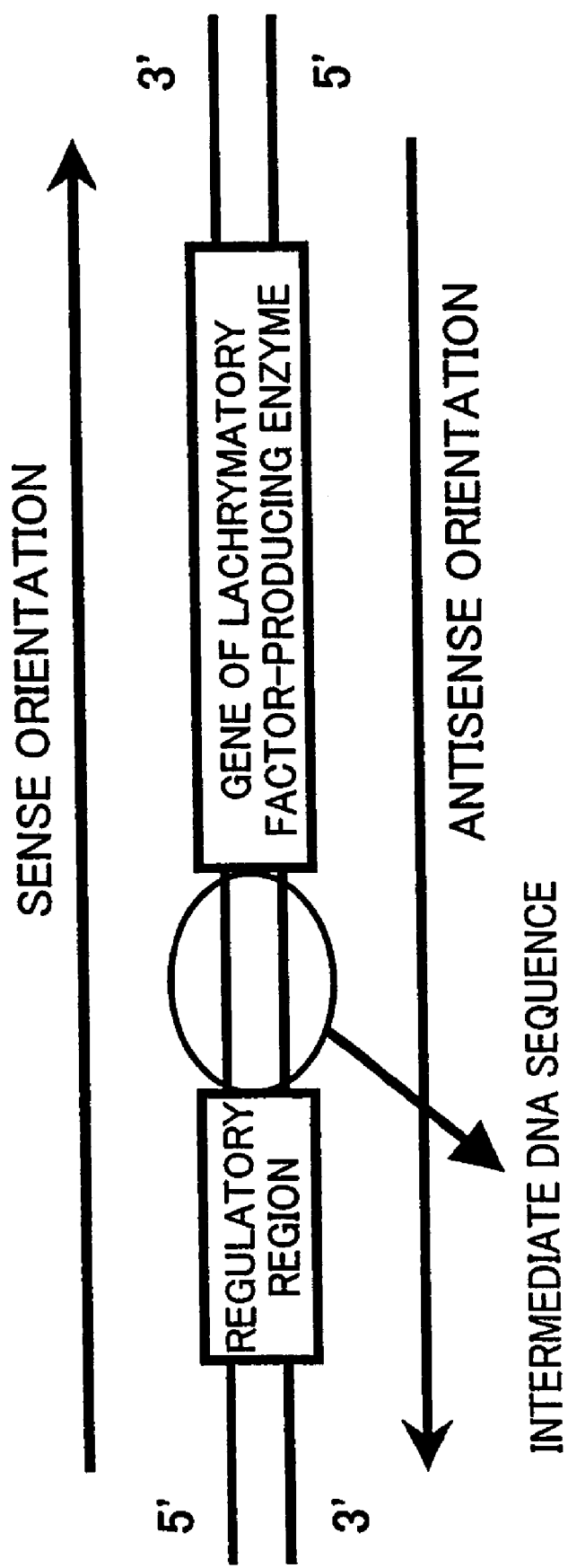
FIG. 1 shows the gene of the lachrymatory factor-producing enzyme and the regulatory region thereof and also the orientation of the intermediate DNA sequence thereof.
Figure 2:
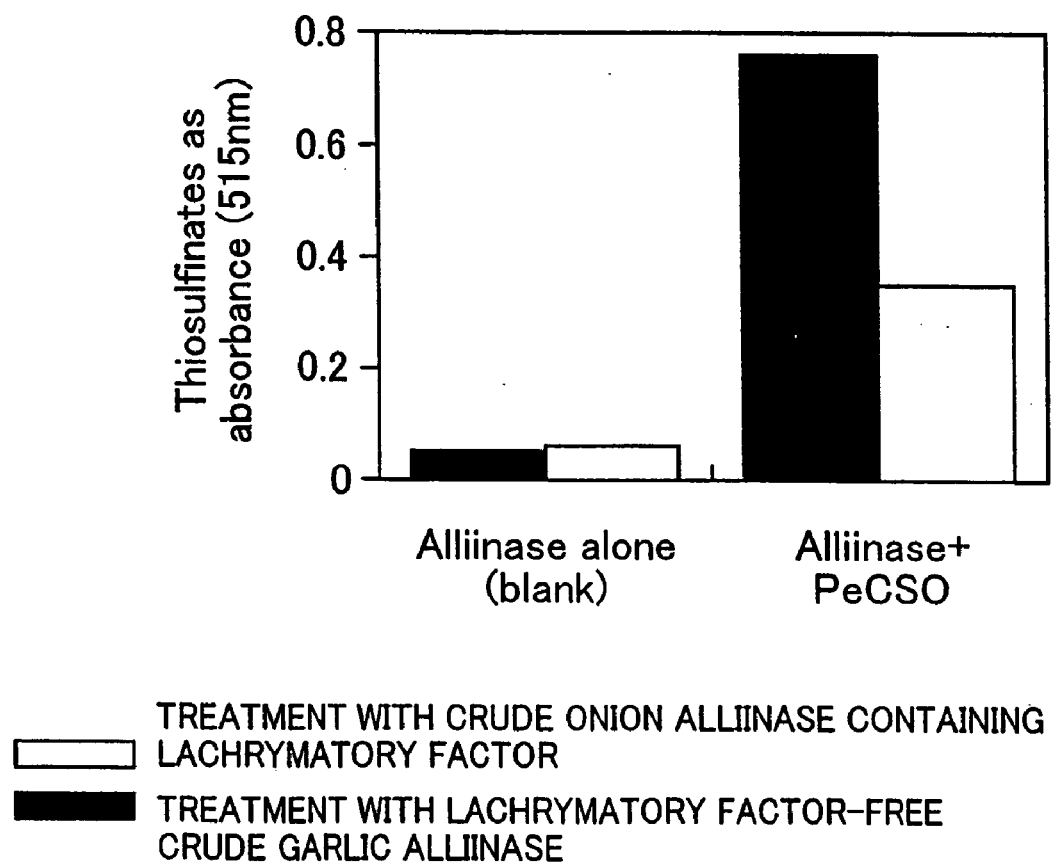
FIG. 2 shows the results of the determination of thiosulfinates obtained in the Referential Example.

The introduction of DNA for repressing the expression of the gene of the lachrymatory factor-producing enzyme of the present invention into vegetables and also the selection and confirmation of the expression-repressed vegetables are concretely conducted by the following methods, which by no means limit the invention.

Example 1

(1) Preparation of Cultured Callus Sample
i. Varieties of Onion

Sen-shyuu-chu-kodakaki onion produced in Japan was selected as the sample.

(ii) Induction of Onion Callus

Full-ripe seeds of onion were surface-sterilized by immersing the seeds in 70% ethanol for 10 minutes and then in a sodium hypochlorite solution having an effective chlorine concentration of 3.3% for 20 minutes and then implanted in a callus induction medium (inorganic salts of MS and vitamins (Murashige, T. & Skoog, F., 1962; Physiol. Plant., 15, 473497), 50 µM fluorophenoxyacetic acid, 1 µM 2-isopentenyladenine, 0.1 M sucrose, 1 g/l casein hydrolyzate, 10 mM N-morpholinoethanesulfonic acid and 2 g/l gellan gum, pH 5.8). After the culture under irradiation with a fluorescent light of 1000 lux at 25° C. for 2 or 3 months, a callus from germinated primary root was obtained. N-Morpholinoethanesulfonic acid added to the callus induction medium was a reagent capable of keeping pH of the medium constant. As for the effect of this reagent, the number of the seeds in which the callus induction occurred was increased and the size of the callus was increased by adding it.

(iii) Multiplication of Onion Callus

The callus obtained by method (ii) described above was passed through a stainless steel mesh having a fineness of 1 mm. 0.2 to 0.4 g of the fine pieces thus obtained were put in 30 ml of callus multiplication medium 1 (inorganic salts of MS and vitamins, 50 µM 4-fluorophenoxyacetic acid, 1 µM 2-isopentenyladenine, 0.1 M sucrose, 1 g/l casein hydrolyzate and 10 mM N-morpholinoethanesulfonic acid, pH 5.8) in a 100 ml Erlenmeyer flask. After the shaking culture at 100 rpm under irradiation with a fluorescent light of 1000 lux at 25° C. for 3 weeks, the multiplied callus was put in 80 ml of callus multiplication medium 2 (inorganic salts of MS and vitamins, 50 µM 4-fluorophenoxyacetic acid, 1 µM 2-isopentenyladenine, 0.2 M sucrose, 1 g/l casein hydrolyzate and 10 mM N-morpholinoethanesulfonic acid, pH 5.8) in a 200 ml Erlenmeyer flask. After the shaking culture at 100 rpm under irradiation with a fluorescent light of 1000 lux at 25° C. for additional 3 to 4 weeks, the multiplied onion callus was obtained.

(2) Preparation of Plasmid (Vector)

A plasmid illustrated below was prepared by integrating a sense strand or antisense strand or both of them of hygromycin-resistant gene (hph) and a part (corresponding to Nos. 102 to 559 in the base sequence of SEQ ID NO.11) of gene (LFS gene) of lachrymatory factor-producing enzyme of onion (LFS) and the first intron of fatty acid desaturase 2(FAD2) gene of *Arabidopsis thaliana* into R-DNA region. Although the insertion of the intron is not indispensable, its effect is known. Namely, by inserting the intron as a spacer between the sense strand and antisense strand, the inverted-repeat DNA sequence comprising the sense strand and antisense strand is stabilized (Smith, N. A. et al., 2000; Nature, 407: 319-320). It is also known that when the sense strand or antisense strand is used alone, the effect of restriction of the gene expression is improved by inserting the intron near the strand (Wesley, S. V. et al., 2001; The Plant Journal, 27(6): 581-590). The sense strand and antisense strand of LFS gene and the intron were amplified by PCR from genome DNA of onion and genome DNA of Arabidopsis thaliana, respectively, with reference to "a method for PCR amplification of genes with a primer with anchor of a restriction enzyme" (Levin, J. Z. et al., 2000; Plant Molecular Biology, 44: 759-775).

(i) Super Binary Plasmid

1. Preparation of Intermediate Vector

Figure 3:
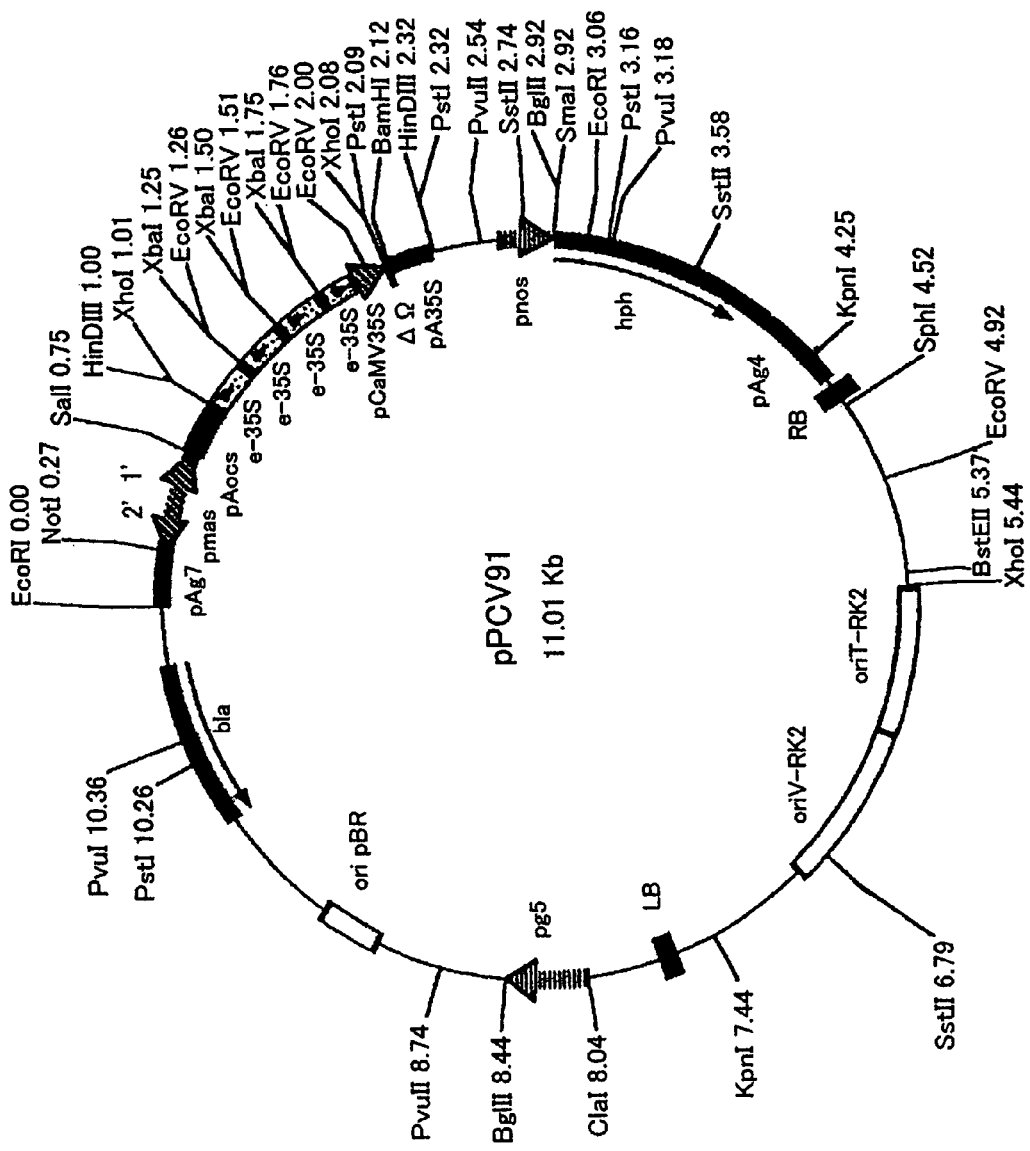
FIG. 3 is a map of pPCV91.

A hygromycin-resistant expression cassette of pPCV91 (FIG. 3) (a fraction obtained by linking a promoter of nopaline synthase (pnos), hygromycin phosphotransferase gene (hph) and polyA signal of gene 4 of *Agrobacterium* Ti plasmid (pAg4)), 35S promoter of cauliflower mosaic virus (CaMV) in pBI121 (purchased from Invitrogen) and nopaline synthase terminator were inserted in this order into a right border side of T-DNA region of super binary intermediate vector pSB11 (Komari, T. et al., 1996; The Plant Journal, 10(1): 165-174). After the insertion, sense strand of onion LFS gene and then intron of FAD2 were inserted between 35S promoter of the vector and terminator of nopaline synthase to obtain a sense intermediate vector. Further, intron of FAD2 and then antisense strand of onion LFS gene were inserted in this order to obtain antisense intermediate vector. Further, sense strand of onion LFS gene, intron of FAD2 and antisense strand of onion LFS gene were inserted in this order to obtain RNAi intermediate vector.

2. Preparation of Super Binary Vector

The intended genes in the three kinds of the intermediate vectors prepared in above process 1 were introduced into super binary acceptor vector pSB1 (Komari, T. et al., 1996; The plant Journal, 10(1): 165-174) by the homologous recombination. Namely, both the intermediate vector and pSB1 had 2.7 kb homologous sequence and the homologous recombination occurred in this region to form a new superbinary vector composed of the intermediate vector and sSB1 connected with each other. The homologous recombination occurs when the intermediate vector previously introduced into *E. coli* is introduced into *Agrobacterium*, into which pSB1 has been introduced, by triple cross technique (Ditta, G et al., 1980; Proc. Natl. Acad. Sci. USA, 77: 7347-7351) which will be stated in paragraph (3). Superbinary vector pSBsense was obtained by the homologous recombination of the sense intermediate vector with pSB1. Superbinary vector pSBantisense was obtained by the homologous recombination of the antisense intermediate vector with pSB1. Superbinary vector pSBRNAi was obtained by the homologous recombination of the RNAi intermediate vector with pSB1.

(ii) Binary Plasmid

A hygromycin-resistant expression cassette of pPCV91 (a fraction obtained by linking a promoter of nopaline synthase (pnos), hygromycin phosphotransferase gene (hph) and polyA signal of gene 4 of *Agrobacterium* Ti plasmid (pAg4)) was inserted between nopaline synthase terminator and 35S promoter of cauliflower mosaic virus (CaMV) in T-DNA region of pBI121. Then β-D-glucuronidase (GUS) gene was removed by the process with a restriction enzyme. The sense strand of onion LFS gene and FAD2 intron were inserted in this order into a part, from which GUS gene had been removed, on the 35S promoter side of cauliflower mosaic virus (CaMV) to obtain binary vector pBIsense. Further, FAD2 intron and antisense strand of onion LFS gene were inserted in this order therein to obtain binary vector pBIantisense. In addition, sense strand of onion LFS gene, FAD2 intron and antisense strand of onion LFS gene were inserted in this order to obtain binary vector pBIRNAi.

(3) Parasitic *Agrobacterium*

*Agrobacterium* LBA4404 (purchased from Invitrogen) obtained by removing T-DNA region from Ti plasmid was used as the parasitic bacterium. LBA4404 is a microorganism having helper plasmid pAL4404 having a perfect virulence region.

Various vectors prepared in above paragraph (2) were introduced into LBA4404 by the triple cross technique for bacteria, and the obtained microorganism was used as *Agrobacterium* for introducing gene into onion callus. When an intermediate super binary vector was to be introduced, LBA4404 (*Agrobacterium* into which super binary acceptor vector pSB1 had been introduced) was used so that the super binary vector could be obtained by the homologous recombination of the intermediate vector and the acceptor vector. In the triple cross technique, the culture media used for selecting *Agrobacterium* into which the intended plasmid had been introduced were AB medium containing spectinomycin (50 μg/ml) (Chilton et al., 1974; Proc. Natl. Acad. Sci, USA, 71: 3672-3676) for the super binary vector, and MinA medium containing kanamycin (400 μg/ml) (Miller, J. H., 1972: Experiments in Molecular Genetics, Cold Spring Harbor Laboratory, New York) for the binary vector. *Agrobacterium* into which plasmid (vector) has been introduced will be referred to under the name of the microorganism followed by the plasmid name in the parentheses such as LBA4404(pSBsense). The following microorganisms were used for introducing the gene into onion callus:

LBA4404(pSBsense), LBA4404(pSBantisense), LBA4404(pSBRNAi), LBA4404(pBIsense), LBA4404 (pBIantisense) and LBA4404(pBIRNAi).

(4) Preparation of *Agrobacterium* Suspension

When LBA4404(pSBsense), LBA4404(pSBantisense) or LBA4404(pSBRNAi) was used, it was inoculated in AB culture medium containing spectinomycin (50 μg/ml), and when LBA4404(pBIsense), LBA4404(pBIantisense) or LBA4404 (pBIRNAi) was used, it was inoculated in MinA culture medium containing kanamycin (400 μg/ml), and it was cultured at 28° C. for 3 or 4 days. The cultured cells were scraped with a spatula and then suspended in an *Agrobacterium* suspension culture medium (inorganic salts of MS and vitamins, 1 μM 2-isopentenyladenine, 0.1 M sucrose, 1 g/l casein hydrolyzate, 10 mM N-morpholinoethanesulfonic acid and 10 mg/l acetosyringone, pH 5.8) and the turbidity (OD600) was controlled at 0.15 to 0.20. The obtained suspension was used for the infection.

(5) Infection of Onion Callus with *Agrobacterium*

The onion multiplication callus prepared in above process (1) was immersed in the above-described *Agrobacterium* suspension for 1.5 to 2 minutes. After the immersion, superfluous cell suspension was removed from the onion callus with a paper towel and the onion callus was placed on MSCO medium (inorganic salts of MS and vitamins, 1 μM 2-isopentenyladenine, 0.1 M sucrose, 10 g/l glucose, 1 g/l casein hydrolyzate, 10 mM N-morpholinoethanesulfonic acid, 10 mg/l acetosyringone and 2 g/l gellan gum, pH 5.8), and cultured in the dark at 25 to 28° C. for 3 to 4 days.

(6) Selection of Transformed Individuals

The onion callus co-cultured with *Agrobacterium* for 3 or 4 days was washed with sterilized water containing 500 mg/l of cefotaxime and then transplanted into 500 mg/l cefotaxime-containing MSSE medium (inorganic salts of MS and vitamins, 1 μM 2-isopentenyladenine, 0.1 M sucrose, 1 g/l casein hydrolyzate, 10 mM N-morpholinoethanesulfonic acid and 2 g/l gellan gum, pH 5.8), cultured under irradiation with a fluorescent light of 3,000 to 4,000 lux at 25° C. for 1 week, and then transferred into MSSE medium containing 250 mg/l cefotaxime and 50 mg/l hygromycin. The culture was continued under irradiation with a fluorescent light of 3,000 to 4,000 lux at 25° C. to select the transformed, re-differentiated cells. The obtained re-differentiated cells were moved to MSSE medium containing 250 mg/l of cefotaxime and 50 mg/l of hygromycin and having a degree of solidification increased by the addition of 5 g/l agar. The culture was continued under the same conditions as that described above to grow the cells. By the increase of the degree of solidification of the medium with agar, the vitrification of the re-differentiated vegetable (i. e. a phenomenon of converting the vegetable tissue into a transparent glass-like tissue and to make the normal growth impossible. This phenomenon is frequently observed in culturing a tissue in test tubes) was controlled and the number of the cells grown as the normal vegetable was increased.

(7) Efficiency of Appearance of Re-Differentiated Cells Resistant to Hygromycin Depending on the Vectors The re-differentiated vegetables resistant to hygromycin appeared from onion callus infected with *Agrobacterium* having various vectors introduced therein (Table 1).

TABLE 1

Efficiency of appearance of re-differentiated vegetables resistant to hygromycin depending on the vector

| Agrobacterium sample | Number of hygromycin-resistant vegetable/number of processed cells (%) |
|---|---|
| LBA4404(pSBsence) | 3/144(2) |
| LBA4404(pSBantisence) | 21/144(15) |
| LBA4404(pSBRNAi) | 62/432(14) |
| LBA4404(pBIsence) | 10/144(7) |
| LBA4404(pBIantisence) | 12/126(10) |
| LBA4404(pBIRNAi) | 24/288(8) |

When the vector used was super binary vector (pSB) having a strong infectious property on vegetables, the rate of appearance of the re-differentiated vegetable resistant to hygromycin was 2 to 15%, and when the vector used was an ordinary binary vector (pBI), the rate of appearance of the re-differentiated vegetable resistant to hygromycin was 7 to 10%. No significant difference in the rate of appearance of the re-differentiated vegetable resistant to hygromycin depending on the difference in the vector was found. The re-differentiated vegetable resistant to hygromycin was obtained by using any vector.

Example 2

A re-differentiated vegetable S obtained from onion callus cocultured with LBA4404(pBIsense) and resistant to hygromycin and also a re-differentiated vegetable A obtained from onion callus cocultured with LBA4404(pBIantisense) and resistant to hygromycin were analyzed as follows:

(1) Analysis of Gene Introduced into Transformed Re-Differentiated Vegetable Body PCR method was conducted to examine whether an intended gene had been introduced into a re-differentiated vegetable body obtained by the selection with hygromycin or not.

(i) Extraction of DNA from Re-Differentiated Vegetable Body Resistant to Hygromycin Leaves of re-differentiated vegetable body resistant to hygromycin were used as the starting material. DNA was extracted from the leaves with DNEASY Plant Mini Kit (a product of QIAGEN Co.) (a DNA purification kit) according to the instruction of DNEASY Plant Mini Kit Handbook attached to the kit.

(ii) Primers for the Detection

A combination of the following 5 kinds of primers was used for PCR to confirm the presence of the introduced gene.

```
                                           (SEQ ID NO. 17)
Primer A: 5'-AATTAAGGGAGTCACGTTATGACCC-3'

(SEQ ID NO. 18)
Primer B: 5'-AGAAACTTCTCGACAGACGTCGC-3'

(SEQ ID NO. 19)
Primer C: 5'-GTGGCAATCCCTTTCACAACCTG-3'

(SEQ ID NO. 20)
Primer D: 5'-TGGAGGGTCCTGAGCACAAG-3'

(SEQ ID NO. 21)
Primer E: 5'-TGCGGGACTCTAATCATAAAAACCCAT-3'
```

Primer A anneals with promoter of nopaline synthase in a introduced gene, and primer B anneals with hygromycin phosphotransferase gene in the introduced genes. By using the combination of primer A and primer B for PCR, the presence of the hygromycin-resistant gene in the introduced genes can be confirmed. 344 bp amplification product is obtained from DNA of the vegetable body containing hygromycin-resistant gene introduced therein.

Primer C anneals with FAD2 intron in the introduced gene, and primer D anneals with LFS gene. By using the combination of primer C and primer D for PCR, the presence of the antisense strand of onion LFS gene in the introduced genes can be confirmed. 326 bp amplification product is obtained from DNA of the vegetable body (vegetable body transformed with LBA4404(pBIantisense)) containing antisense strand of onion LFS gene introduced therein.

Primer E anneals with nopaline synthase terminator in the introduced gene. By using the combination of primer C and primer E for PCR, the absence of the antisense strand of LFS gene in onion DNA in which antisense strand-free construct or, in other words, construct composed of the sense strand and intron is introduced can be confirmed. 360 bp amplification product is obtained from DNA of the onion vegetable body (LBA4404(pBIsense)) containing antisense strand-free construct introduced therein.

(iii) PCR

PCR was conducted by using AMPLITAQ GOLD(R) (a taq polymerase) & 10× PCR Buffer II & MgCl$_2$ Solution with dNTP (a product of Applied Biosystems Co.) by the following method:

0.125 µl of AMPLITAQ GOLD (5 U/µl), 2.5 µl of dNTPs Mix (2 mM each) and 1.5 µl of MgCl$_2$ solution (25 mM) were added to 2.5 µl of 10× PCR Buffer II. Then 0.5 µM (final concentration) of each of a pair of primers and template DNA were added to the obtained mixture. Sterilized ultra pure water was added thereto to make the total amount 25 µl. The solution for the reaction was fed into a 0.2 ml microtube. After the enzymatic activation (94° C., 10 minutes) with a thermal cycler GENE AMP PCR System 2400 (Applied Biosystems Co.) (a thermal cycler for PCR amplification), the reactions of denaturation (94° C., 1 minute)/annealing (58° C., 1 minute)/elongation (72° C., 1 minute) were repeated 40 times. The reaction was completed by the final elongation (72° C., 7 minutes). The obtained PCR reaction mixture was subjected to the electrophoresis with 2% agarose gel containing ethidium bromide and then analyzed with FLUORIMAGER 595 (fluorescent image analyzer of Amercham Bioscience Co.).

(iv) Results of the Confirmation of Gene Introduced into Re-Differentiated Vegetable Body Resistant to Hygromycin The presence of introduced gene in re-differentiated vegetable body S resistant to hygromycin was confirmed to obtain the results shown in Table 2. Namely, 344 bp amplification product obtained by the combination of primers A and B, and 360 bp amplification product obtained by the combination of primers C and E were confirmed. DNA at both ends of the introduction construct could be confirmed in DNA of the re-differentiated vegetable body S. It was thus found that the re-differentiated vegetable body S was the transformed vegetable body.

TABLE 2

Results of the confirmation of gene introduced into re-differentiated vegetable body S resistant to hygromycin

| Vegetable body | Agrobacterium | Primers A and B, 344 bp | Primers C and E, 360 bp |
|---|---|---|---|
| S | LBA4404(pBIsense) | o | o | o: The amplification product was recognized.

The presence of introduced gene in re-differentiated vegetable body A resistant to hygromycin was confirmed to obtain the results shown in Table 3. Namely, 344 bp amplification product obtained by the combination of primers A and B, and 326 bp amplification product obtained by the combination of primers C and D were confirmed. DNA at both ends of the introduction construct could be confirmed in DNA of the re-differentiated vegetable body A. It was thus found that the re-differentiated vegetable body A was the transformed vegetable body.

TABLE 3

Results of the confirmation of gene introduced into re-differentiated vegetable body A resistant to hygromycin

| Vegetable body | Agrobacterium | Primers A and B, 344 bp | Primers C and D, 326 bp |
|---|---|---|---|
| A | LBA4404(pBIantisense) | o | o | o: The amplification product was recognized.

(2) Determination of LFS Activity of Transformed Re-Differentiated Vegetable Body Each whole shoot (leaves and stems) of each of the transformed re-differentiated vegetable bodies S and A were cut and analyzed in order to avoid uneven results of the determination depending on the sites of individuals. 6 vegetable bodies regenerated from the onion callus which was not coc-ultured with Agrobacterium were also subjected to the analysis as controls. PBS (137 mM NaCl, 8.10 mM Na$_2$HPO$_4$.12H$_2$O, 2.68 mM KCl and 1.47 mM KH$_2$PO$_4$) was added to the shoots cut off as described above. After the homogenization followed by the centrifugation at 6,000× g for 5 minutes, the supernatant was taken as the enzyme extract. 40 µl of garlic alliinase (50 units/ml) and 20 µl of PeCSO (trans-(+)-S-(1-propenyl)-L-cysteine sulfoxide) solution (20 mg/ml) were added to 10 µl of the enzyme extract. The vessel was tightly closed and they were reacted at room temperature for 3 minutes. 1 µl of the reaction mixture was poured into HPLC to determine the peak area of the lachrymatory factor. In the analysis, ODS column (4.6 φ×250 mm) (a product of Senshuu Kagaku Co.) was used. 30% (v/v) acidic methanol was used as the mobile phase, and the determination was conducted at a flow rate of 0.6 ml/min, column temperature of 35° C. and detection wave length of 254 nm. The obtained value was converted to the peak area of the lachrymatory factor per mg of the total protein in the enzyme extract. The peak area thus calculated was taken as the LFS activity.

The total amount of protein in the enzyme extract was determined by Bradford method (Bradford, M. M., 1976, Anal. Biochem., 72, 248-254) with BSA (Bovine Serum Albumin) as the standard.

Figure 4:
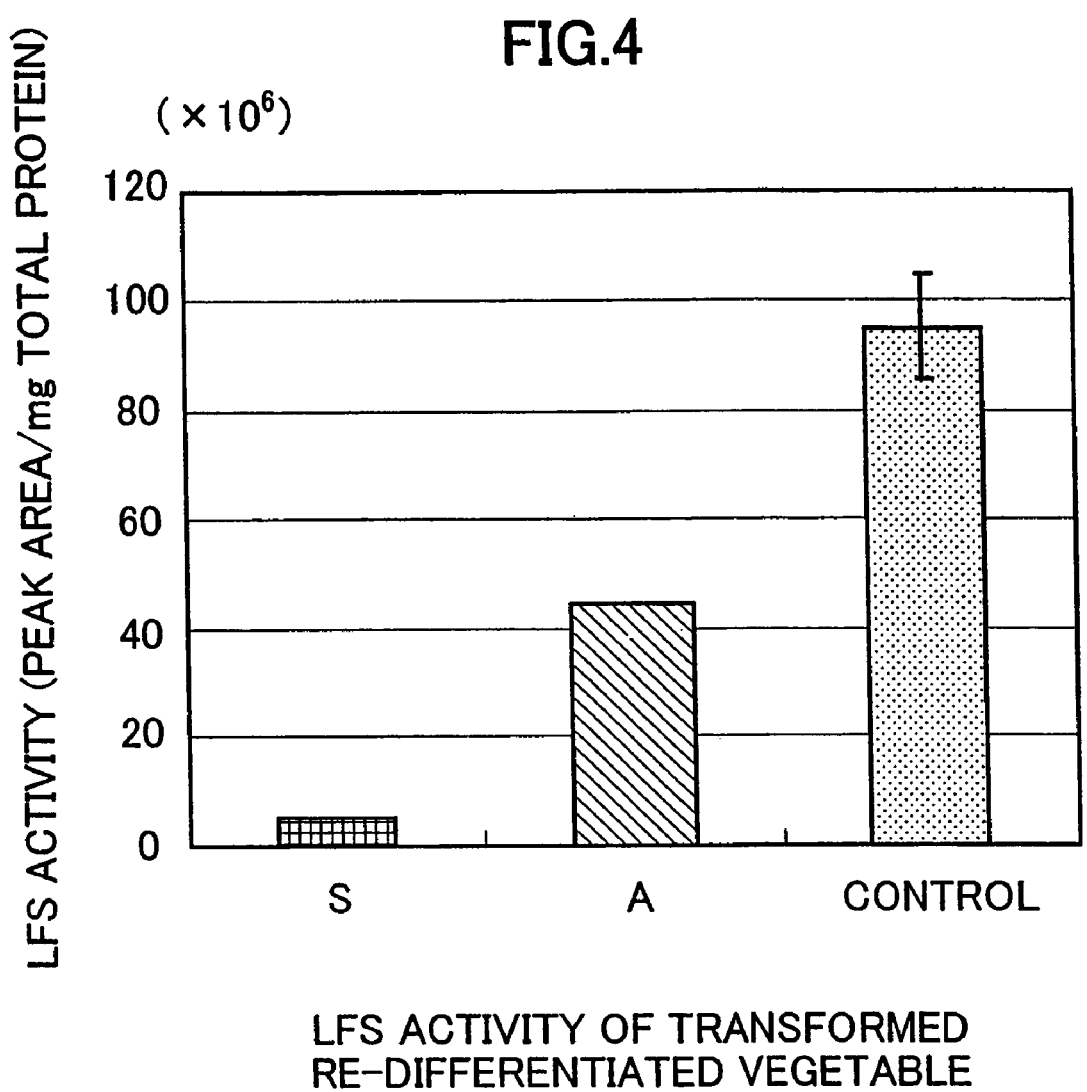
FIG. 4 shows LFS activity of six transformed re-differentiated onions obtained by co-culture with LBA4404 (pBIsense) (identified as vegetable body "S") and six transformed re-differentiated onions obtained by co-culture with LBA4404(pBIantisense) (identified as vegetable body "A") as compared to six control onions, which were not cocultured with *Agrobacterium*.

LFS activity of each of the 6 control vegetable bodies regenerated from onion callus which had not been co-cultured with Agrobacterium was compared with LFS activity of each of transformed re-differentiated vegetable bodies S and A to obtain the results shown in FIG. 4. LFS activity of each of the 6 control vegetable bodies was shown in terms of the average of them and the standard error thereof was also shown.

LFS activity of the transformed re-differentiated vegetable S obtained by the co-culture with LBA4404(pBIsense) was as low as about 5% based on the control. Thus, LFS activity was remarkably repressed to about ¹⁄₂₀. LFS activity of the transformed re-differentiated vegetable A obtained by the co-culture with LBA4404(pBIantisense) was about 47% based on the control. Thus, LFS activity was repressed to about a half. Although the extent of the repression of LFS activity was various, the LFS activity was repressed in all the transformed re-differentiated vegetables.

(iv) Determination of LFS Protein in Transformed Regenerated Vegetables

The amount of LFS protein in the transformed regenerated vegetables was determined by western blotting method.

The primary antibody used for the immunostaining was prepared by immunizing a rat with recombinant LFS expressed in E. coli as the antigen. The immunization was conducted 6 times in total at intervals of 2 weeks. In the first immunization, about 0.2 mg of recombinant LFS was used. The whole blood was taken 11 weeks after the initiation of the immunization to prepare anti-LFS antiserum. The obtained anti-LFS antiserum was precipitated with 50% saturated ammonium sulfate. The precipitate was dissolved and dialyzed with 20 mM sodium phosphate buffer (pH 7.0). Finally, antiLFS antibody affinity-purified with an LFS linking column was used as the primary antibody. Other blocking reagent, secondary antibody, tertiary antibody and fluorescent substrate used were those of ECF Western Blotting Kit (Amercham Bioscience Co.).

The protein concentration in the enzyme extract prepared in above-described step (2) was adjusted to 40 µg/ml. 15 µl of this product was applied to a well of SDS polyacrylamide gel. After the electrophoresis followed by the blotting on PVDF membrane by semi-dry method, the membrane was immersed in a blocking solution and shaken at 4° C. overnight or at room temperature for 1 hour. The blocking solution was prepared by dissolving a membrane blocking agent in PBS-T (137 mM NaCl, 8.10 mM Na$_2$HPO$_4$.12H$_2$O, 2.68 mM KCl, 1.47 mM KH$_2$PO$_4$, 0.1% (w/v) Tween 20) to obtain the 5% (w/v) solution. After the blocking, the membrane was washed with PBS-T, immersed in an antiLFS antibody (primary antibody) solution diluted to 1/250 with PBS-T and then shaken at room temperature for 1 hour. After the completion of the reaction, the membrane was washed with PBS-T, immersed in a solution of anti-rabbit Ig, fluorescein-linked whole antibody (secondary antibody) diluted to 1/600 with PBS-T and then shaken at room temperature for 1 hour. After the completion of the reaction, the membrane was washed with PBS-T, immersed in a solution of Anti-fluorescein alkaline phosphatase conjugate (tertiary antibody) solution diluted to 1/2500 with PBS-T and then shaken at room temperature for 1 hour. After the completion of the reaction followed by washing with PBS-T, a fluorescent substrate solution was applied to the membrane. The membrane was left to stand at room temperature for 20 minutes to carry out the reaction. The fluorescent substrate solution was prepared by dissolving 36 mg of ECF substrate (fluorescent substrate) in 60 ml of ECF substrate dilution buffer. After the completion of the reaction, the fluorescent substrate on the membrane was completely dried and the fluorescent signal was detected with FLUORIMAGER 595 (Amercham Bioscience Co.). From the obtained digital image, the fluorescent signal (volume) of LFS specific band was determined with IMAGEQUANT software (Amercham Bioscience Co.) (software for quantifying fluorescent images). The obtained value was converted into a fluorescent signal amount of LFS specific band per mg of the total protein in the enzyme extract, and this amount was shown as the amount of LFS protein.

Figure 5:
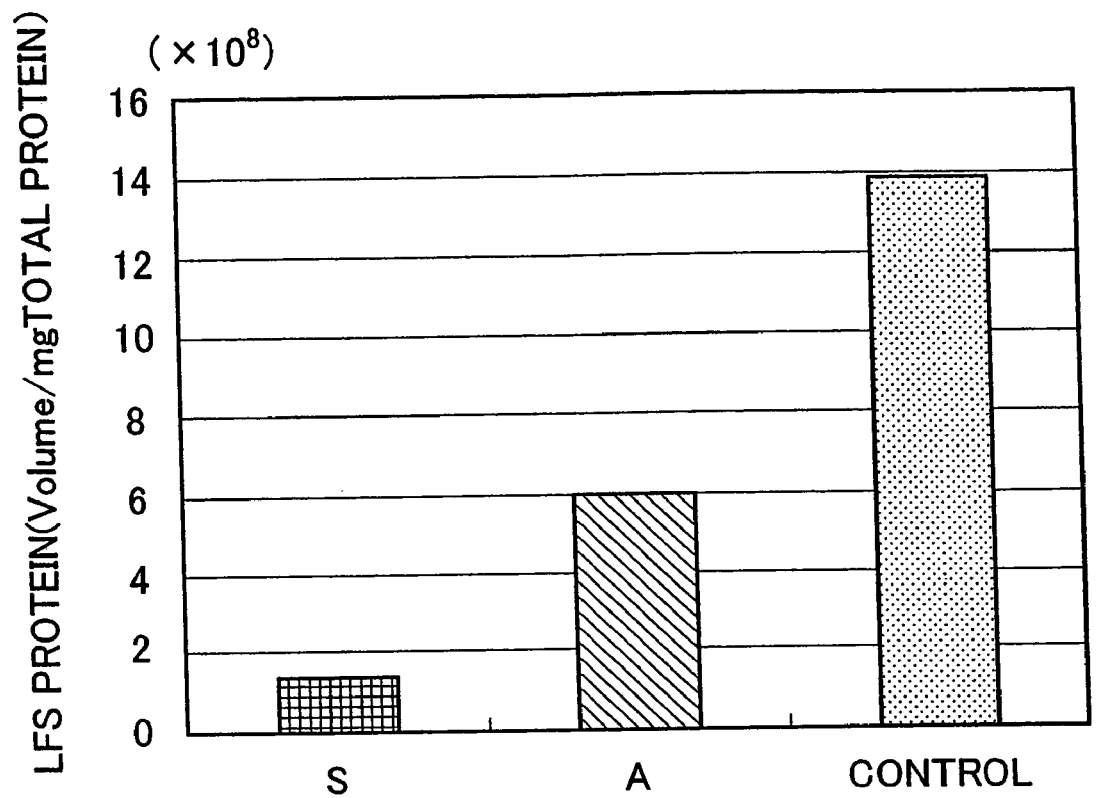
FIG. 5 shows the amount of LFS protein of six transformed re-differentiated onions obtained by co-culture with LBA4404(pBIsense) (identified as vegetable body "S") and six transformed re-differentiated onions obtained by co-culture with LBA4404(pBIantisense) (identified as vegetable body "A") as compared to six control onions, which were not cocultured with *Agrobacterium*.

The amount of LFS protein of the control vegetable bodies regenerated from onion callus which had not been co-cultured with *Agrobacterium* was compared with the amount of LFS protein of each of transformed re-differentiated vegetable bodies S and A to obtain the results shown in FIG. 5.

The amount of LFS protein of the transformed re-differentiated vegetable S obtained by the co-culture with LBA4404 (pBIsense) was as small as about 10% based on that of the control. This fact indicates that the expression was remarkably repressed. On the other hand, the amount of LFS protein of the transformed re-differentiated vegetable A obtained by the co-culture with LBA4404(pBIantisense) was about 43% based on that of the control. This fact indicated that the expression of LFS protein was repressed to about a half. Although the extent of the repression of the amount of the LFS protein was various, the expression of the LFS protein was repressed in all the transformed re-differentiated vegetables.

INDUSTRIAL APPLICABILITY

According to the present invention, it is possible to provide DNA and RNA designed on the basis of the sequence of a gene of an enzyme for forming the lachrymatory factor from a precursor of this factor, a vector required for introducing the expression-repressing DNA of the gene of the lachrymatory factor-producing enzyme into a vegetable, a method for repressing the expression of the gene of the lachrymatory factor-producing enzyme by using them and also a vegetable in which the expression of the gene of the lachrymatory factor-producing enzyme is repressed. Accordingly, the expression of the gene can be thus repressed. Other advantages of the present invention are that because the formation of the lachrymatory factor can be essentially repressed and no influence of other external factors is exerted on the quality and quantity of the precursor of the lachrymatory factor, the quality of anion is not lowered and that the expression of the gene can be repressed in a period shorter than that in ordinary techniques of breeding vegetables which are free from the genetic engineering.

According to the present invention, the expression of the gene of the lachrymatory factor-producing enzyme can be repressed to also control the amount of the protein in the enzyme. Thus, a vegetable having a lowered activity of the enzyme can be obtained. It is also possible to obtain a vegetable having an increased amount of a thiosulfinates compound, which is a cause of the flavor and which has an anti-asthmatic effect, and also a high quality of taste and containing a large amount of components expected to have a physiological activity.

Further, according to the present invention, it is possible to produce a vegetable having a lachrymatory factor-producing enzymatic activity repressed to less than about 50% or less than about 10% based on that of a non-transformed control vegetable. It is also possible to produce a vegetable having a protein content of the lachrymatory factor-producing enzyme repressed to less than about 50% or less than about 15% based on that of a non-transformed control vegetable. It is further possible to produce a vegetable having a desirable activity of the lachrymatory factor-producing enzyme by varying the level of repressing the expression of the gene of the lachrymatory factor-producing enzyme. In addition, it is possible to provide an *allium* vegetable having the above-described properties.

What is claimed is:

1. A construct comprising the isolated nucleic acid of SEQ ID NO:11 operably linked to a promoter in either sense or antisense orientation.

2. A vector containing the construct of claim 1.

3. A method for transformation; said method comprising introducing the construct of claim 1 into an *allium* plant or plant cell.

4. An *allium* plant transformed with the construct of claim 1.

5. An *allium* plant transformed with the vector of claim 2.

6. The plant of claim 4 which has a lachrymatory factor content lower than that of a non-transformed control plant.

7. The plant of claim 5 which has a lachrymatory factor content lower than that of a non-transformed control plant.

8. A construct comprising a promoter operably linked to a fragment of SEQ ID NO:11 having at least 22 contiguous bases of SEQ ID NO:11 and further comprising a nucleic acid that is complementary to the fragment such that the construct is effective for suppressing expression of an endogenous LFS gene, wherein a vegetable of genus *Allium* transformed with the construct has a lower level of lachrymatory factor compared to a non-transformed control vegetable of the same species.

9. A vector containing the construct of claim 8.

10. A method for transformation; said method comprising introducing the construct of claim 8 into an *Allium* plant cell.

11. An *Allium* plant transformed with the construct of claim 8.

* * * * *

UNITED STATES PATENT AND TRADEMARK OFFICE
CERTIFICATE OF CORRECTION

PATENT NO. : 7,452,988 B2  Page 1 of 1
APPLICATION NO. : 10/932950
DATED : November 18, 2008
INVENTOR(S) : Imai et al.

It is certified that error appears in the above-identified patent and that said Letters Patent is hereby corrected as shown below:

On the title page item (75), replace "Tsunchiro Kamata" with "Yasuhiro Kamata".

At column 1, line 43, the printed patent reads "...referred to as LP) is generated..."; the printed patent should read "...referred to as LF) is generated...".

At column 9, line 57, the printed patent reads "...used for site-specifically cleaving RBA."; the printed patent should read "...used for site-specifically cleaving RNA.".

Signed and Sealed this

Twenty-fourth Day of February, 2009

JOHN DOLL
*Acting Director of the United States Patent and Trademark Office*

SEQUENCE LISTING

```
<160> NUMBER OF SEQ ID NOS: 21

<210> SEQ ID NO 1
<211> LENGTH: 739
<212> TYPE: DNA
<213> ORGANISM: Allium fistulosum L.
<220> FEATURE:
<221> NAME/KEY: CDS
<222> LOCATION: (58)..(564)
<223> OTHER INFORMATION: P
<220> FEATURE:
<221> NAME/KEY: polyA_site
<222> LOCATION: (723)..(739)
<223> OTHER INFORMATION: P

<400> SEQUENCE: 1
cacaaattca aaactcacat ttcgttaaat ttagaagaat tattcaatcg ggaaaaa        57 atg gag cta aat cct ggt gcg cct gct gta gtc act gat ggt gct aac    105
Met Glu Leu Asn Pro Gly Ala Pro Ala Val Val Thr Asp Gly Ala Asn
1               5                   10                  15 gga gct cga aaa tgg agc ggc aaa gtc cat gct ttg ctt cca aat tca    153
```

```
                Gly Ala Arg Lys Trp Ser Gly Lys Val His Ala Leu Leu Pro Asn Ser
                                20                  25                  30 aag cca gag caa gca tgg agg cta cta aag gac ttt att aac ctt cac       201
Lys Pro Glu Gln Ala Trp Arg Leu Leu Lys Asp Phe Ile Asn Leu His
            35                  40                  45 aag atc atg cct tcg ttg tca gtc tgt gaa ctg gta gaa ggt aag gcc       249
Lys Ile Met Pro Ser Leu Ser Val Cys Glu Leu Val Glu Gly Lys Ala
50                  55                  60 aat gtt gtt ggt tgt gtt cgc cac gtt aaa ggt ata atg cac cca ata       297
Asn Val Val Gly Cys Val Arg His Val Lys Gly Ile Met His Pro Ile
65                  70                  75                  80 gaa gag gaa ttt tgg gcc aag gag aag ctg gtg gca ctg gat aat aag       345
Glu Glu Glu Phe Trp Ala Lys Glu Lys Leu Val Ala Leu Asp Asn Lys
                85                  90                  95 aac atg agc tac agt tat att ttt act gag tgt ttt aca ggg ttc gag       393
Asn Met Ser Tyr Ser Tyr Ile Phe Thr Glu Cys Phe Thr Gly Phe Glu
            100                 105                 110 gat tac acg gct acc atg caa ata gtg gag gga cct gag cac aag gga       441
Asp Tyr Thr Ala Thr Met Gln Ile Val Glu Gly Pro Glu His Lys Gly
            115                 120                 125 tgt aga ttt gac tgg tct ttt cag tgc aag tat atc gag ggt atg act       489
Cys Arg Phe Asp Trp Ser Phe Gln Cys Lys Tyr Ile Glu Gly Met Thr
130                 135                 140 gaa tct gca ttc gcc gag att ctg cag cat tgg gct act gaa att ggt       537
Glu Ser Ala Phe Ala Glu Ile Leu Gln His Trp Ala Thr Glu Ile Gly
145                 150                 155                 160 cag aaa atc gaa gag att tgc aat gct tgattatgaa tatcggttat            584
Gln Lys Ile Glu Glu Ile Cys Asn Ala
                165 ggtttggtgc attgtgtgtg ttttaaaccg tatcttgtga tgtaataaag taacgtaata    644 tgtgcacgta ataagtaagc ctgagtgttg tgtgttcaat aaaaaagaac ttgcttttg     704 catgttctaa tgcttttcaa aaaaaaaaaa aaaaa                                739

<210> SEQ ID NO 2
<211> LENGTH: 169
<212> TYPE: PRT
<213> ORGANISM: Allium fistulosum L.

<400> SEQUENCE: 2

Met Glu Leu Asn Pro Gly Ala Pro Ala Val Val Thr Asp Gly Ala Asn
1               5                   10                  15

Gly Ala Arg Lys Trp Ser Gly Lys Val His Ala Leu Leu Pro Asn Ser
                20                  25                  30

Lys Pro Glu Gln Ala Trp Arg Leu Leu Lys Asp Phe Ile Asn Leu His
            35                  40                  45

Lys Ile Met Pro Ser Leu Ser Val Cys Glu Leu Val Glu Gly Lys Ala
50                  55                  60

Asn Val Val Gly Cys Val Arg His Val Lys Gly Ile Met His Pro Ile
65                  70                  75                  80

Glu Glu Glu Phe Trp Ala Lys Glu Lys Leu Val Ala Leu Asp Asn Lys
                85                  90                  95

Asn Met Ser Tyr Ser Tyr Ile Phe Thr Glu Cys Phe Thr Gly Phe Glu
            100                 105                 110

Asp Tyr Thr Ala Thr Met Gln Ile Val Glu Gly Pro Glu His Lys Gly
            115                 120                 125

Cys Arg Phe Asp Trp Ser Phe Gln Cys Lys Tyr Ile Glu Gly Met Thr
130                 135                 140
```

```
Glu Ser Ala Phe Ala Glu Ile Leu Gln His Trp Ala Thr Glu Ile Gly
145                 150                 155                 160

Gln Lys Ile Glu Glu Ile Cys Asn Ala
                165
```

<210> SEQ ID NO 3
<211> LENGTH: 682
<212> TYPE: DNA
<213> ORGANISM: Allium fistulosum L.
<220> FEATURE:
<221> NAME/KEY: CDS
<222> LOCATION: (1)..(507)
<223> OTHER INFORMATION: P
<220> FEATURE:
<221> NAME/KEY: polyA_site
<222> LOCATION: (666)..(682)
<223> OTHER INFORMATION: P

<400> SEQUENCE: 3

```
atg gag cta aat cct ggt gcg cct gct gta gtc act gat ggt gct aac      48
Met Glu Leu Asn Pro Gly Ala Pro Ala Val Val Thr Asp Gly Ala Asn
1               5                   10                  15 gga gct cga aaa tgg agc ggc aaa gtc cat gct ttg ctt cca aat tca      96
Gly Ala Arg Lys Trp Ser Gly Lys Val His Ala Leu Leu Pro Asn Ser
            20                  25                  30 aag cca gag caa gca tgg agg cta cta aag gac ttt att aac ctt cac     144
Lys Pro Glu Gln Ala Trp Arg Leu Leu Lys Asp Phe Ile Asn Leu His
        35                  40                  45 aag atc atg cct tcg ttg tca gtc tgt gaa ctg gta gaa ggt gag gcc     192
Lys Ile Met Pro Ser Leu Ser Val Cys Glu Leu Val Glu Gly Glu Ala
    50                  55                  60 aat gtt gtt ggt tgt gtt cgc cac gtt aaa ggt ata atg cac cca ata     240
Asn Val Val Gly Cys Val Arg His Val Lys Gly Ile Met His Pro Ile
65                  70                  75                  80 gaa gag gaa ttt tgg gcc aag gag aag ctg gtg gca ctg gat aat aag     288
Glu Glu Glu Phe Trp Ala Lys Glu Lys Leu Val Ala Leu Asp Asn Lys
                85                  90                  95 aac atg agc tac agt tat att ttt act gag tgt ttt aca ggg ttc gag     336
Asn Met Ser Tyr Ser Tyr Ile Phe Thr Glu Cys Phe Thr Gly Phe Glu
            100                 105                 110 gat tac acg gct acc atg caa ata gtg gag gga cct gag cac aag gga     384
Asp Tyr Thr Ala Thr Met Gln Ile Val Glu Gly Pro Glu His Lys Gly
        115                 120                 125 tgt aga ttt gac tgg tct ttt cag tgc aag tat atc gag ggt atg act     432
Cys Arg Phe Asp Trp Ser Phe Gln Cys Lys Tyr Ile Glu Gly Met Thr
    130                 135                 140 gaa tct gca ttc gcc gag att ctg cag cat tgg gct act gaa att ggt     480
Glu Ser Ala Phe Ala Glu Ile Leu Gln His Trp Ala Thr Glu Ile Gly
145                 150                 155                 160 cag aaa atc gaa gag att tgc aat gct tgattatgaa tatcggttat          527
Gln Lys Ile Glu Glu Ile Cys Asn Ala
                165 ggtttggtgc attgtgtgtg ttttaaaccg tatcttgtga tgtaataaag taacgtaata   587 tgtgcacgta ataagtaagc ctgagtgttg tgtgttcaat aaaaaagaac ttgcttttg    647 catgttctaa tgcttttcaa aaaaaaaaaa aaaaa                             682
```

<210> SEQ ID NO 4
<211> LENGTH: 169
<212> TYPE: PRT
<213> ORGANISM: Allium fistulosum L.

<400> SEQUENCE: 4

```
Met Glu Leu Asn Pro Gly Ala Pro Ala Val Val Thr Asp Gly Ala Asn
1               5                   10                  15

Gly Ala Arg Lys Trp Ser Gly Lys Val His Ala Leu Leu Pro Asn Ser
            20                  25                  30

Lys Pro Glu Gln Ala Trp Arg Leu Leu Lys Asp Phe Ile Asn Leu His
        35                  40                  45

Lys Ile Met Pro Ser Leu Ser Val Cys Glu Leu Val Glu Gly Glu Ala
    50                  55                  60

Asn Val Val Gly Cys Val Arg His Val Lys Gly Ile Met His Pro Ile
65                  70                  75                  80

Glu Glu Glu Phe Trp Ala Lys Glu Lys Leu Val Ala Leu Asp Asn Lys
                85                  90                  95

Asn Met Ser Tyr Ser Tyr Ile Phe Thr Glu Cys Phe Thr Gly Phe Glu
            100                 105                 110

Asp Tyr Thr Ala Thr Met Gln Ile Val Glu Gly Pro Glu His Lys Gly
        115                 120                 125

Cys Arg Phe Asp Trp Ser Phe Gln Cys Lys Tyr Ile Glu Gly Met Thr
    130                 135                 140

Glu Ser Ala Phe Ala Glu Ile Leu Gln His Trp Ala Thr Glu Ile Gly
145                 150                 155                 160

Gln Lys Ile Glu Glu Ile Cys Asn Ala
                165
```

<210> SEQ ID NO 5
<211> LENGTH: 730
<212> TYPE: DNA
<213> ORGANISM: Allium chinense L.
<220> FEATURE:
<221> NAME/KEY: CDS
<222> LOCATION: (54)..(560)
<223> OTHER INFORMATION: P
<220> FEATURE:
<221> NAME/KEY: polyA_site
<222> LOCATION: (715)..(730)
<223> OTHER INFORMATION: P

<400> SEQUENCE: 5

```
cacaattcaa actcactttt cgttatattt agaagattac ccaatcagaa aaa atg        56
                                                          Met
                                                          1 gag caa aat tct ggt acg ctt gct gta gtc act gat ggt gct aaa gga      104
Glu Gln Asn Ser Gly Thr Leu Ala Val Val Thr Asp Gly Ala Lys Gly
        5                   10                  15 gct gca aaa tgg aga ggc aaa gtc cat gct ttg ctt cca aat aca aaa     152
Ala Ala Lys Trp Arg Gly Lys Val His Ala Leu Leu Pro Asn Thr Lys
            20                  25                  30 cca gag caa gca tgg aca cta cta aaa gac ttt att aac ctt cac aag      200
Pro Glu Gln Ala Trp Thr Leu Leu Lys Asp Phe Ile Asn Leu His Lys
        35                  40                  45 atc atg cct tcg ttg tca gtt tgt gaa ctg gtt gaa ggc gag gcc aat      248
Ile Met Pro Ser Leu Ser Val Cys Glu Leu Val Glu Gly Glu Ala Asn
    50                  55                  60              65 gtt gtt ggt tgt gtt cgc cac gtt aaa ggt ata atg cac cca atg gaa     296
Val Val Gly Cys Val Arg His Val Lys Gly Ile Met His Pro Met Glu
                70                  75                  80 gag gaa ttt tgg gcc aag gag aag ctg gtt gca ctg gat gat aag aac      344
Glu Glu Phe Trp Ala Lys Glu Lys Leu Val Ala Leu Asp Asp Lys Asn
        85                  90                  95
```

```
atg agc tgt agt tat att ttt gtt gag tgt ttt aca ggg tac gag gat      392
Met Ser Cys Ser Tyr Ile Phe Val Glu Cys Phe Thr Gly Tyr Glu Asp
        100                 105                 110 tac aca gct acc atg caa ata gtg gag gga tct gag cac aag gga tgt      440
Tyr Thr Ala Thr Met Gln Ile Val Glu Gly Ser Glu His Lys Gly Cys
    115                 120                 125 aga ttt gac tgg tct ttt cag tgt aag tat atc gag ggt atg act gaa      488
Arg Phe Asp Trp Ser Phe Gln Cys Lys Tyr Ile Glu Gly Met Thr Glu
130                 135                 140                 145 tct gca ttc acc gat gtt ctg cag cat tgg gct act gag att ggt cag      536
Ser Ala Phe Thr Asp Val Leu Gln His Trp Ala Thr Glu Ile Gly Gln
                150                 155                 160 aaa att gaa gag att tgc aat gct tgatcatgaa taccggttat gttgtgatgc      590
Lys Ile Glu Glu Ile Cys Asn Ala
                165 attgtgtctg ttttaatccc tatcttgtga tttaataatg taacgtaata tgcatgtaat      650 aagtaagccg agtgttgtgt tttcaataaa atagaatttg cttttgcaag ttctaatgct      710 tttcaaaaaa aaaaaaaaaa                                                 730

<210> SEQ ID NO 6
<211> LENGTH: 169
<212> TYPE: PRT
<213> ORGANISM: Allium chinense L.

<400> SEQUENCE: 6

Met Glu Gln Asn Ser Gly Thr Leu Ala Val Val Thr Asp Gly Ala Lys
1               5                   10                  15

Gly Ala Ala Lys Trp Arg Gly Lys Val His Ala Leu Leu Pro Asn Thr
            20                  25                  30

Lys Pro Glu Gln Ala Trp Thr Leu Leu Lys Asp Phe Ile Asn Leu His
        35                  40                  45

Lys Ile Met Pro Ser Leu Ser Val Cys Glu Leu Val Glu Gly Glu Ala
    50                  55                  60

Asn Val Val Gly Cys Val Arg His Val Lys Gly Ile Met His Pro Met
65                  70                  75                  80

Glu Glu Glu Phe Trp Ala Lys Glu Lys Leu Val Ala Leu Asp Asp Lys
                85                  90                  95

Asn Met Ser Cys Ser Tyr Ile Phe Val Glu Cys Phe Thr Gly Tyr Glu
            100                 105                 110

Asp Tyr Thr Ala Thr Met Gln Ile Val Glu Gly Ser Glu His Lys Gly
        115                 120                 125

Cys Arg Phe Asp Trp Ser Phe Gln Cys Lys Tyr Ile Glu Gly Met Thr
    130                 135                 140

Glu Ser Ala Phe Thr Asp Val Leu Gln His Trp Ala Thr Glu Ile Gly
145                 150                 155                 160

Gln Lys Ile Glu Glu Ile Cys Asn Ala
                165

<210> SEQ ID NO 7
<211> LENGTH: 739
<212> TYPE: DNA
<213> ORGANISM: Allium cepa L.
<220> FEATURE:
<221> NAME/KEY: CDS
<222> LOCATION: (55)..(561)
<223> OTHER INFORMATION: P
<220> FEATURE:
<221> NAME/KEY: polyA_site
<222> LOCATION: (724)..(739)
```

<223> OTHER INFORMATION: P

<400> SEQUENCE: 7

```
acacaattca gactcacatt acgttatatc aagaagattg tccaatcaga aaaa atg        57
                                                              Met
                                                              1 gag cta aat cct ggt gca cct gct gta gtc gct gat agt gct aac gga       105
Glu Leu Asn Pro Gly Ala Pro Ala Val Val Ala Asp Ser Ala Asn Gly
        5                  10                  15 gct cga aaa tgg agc ggc aaa gtc cat gct ttg ctt cca aat aca aag       153
Ala Arg Lys Trp Ser Gly Lys Val His Ala Leu Leu Pro Asn Thr Lys
     20                  25                  30 cca gag caa gca tgg aca cta cta aaa gac ttt att aac ctt cac aag       201
Pro Glu Gln Ala Trp Thr Leu Leu Lys Asp Phe Ile Asn Leu His Lys
 35                  40                  45 gtc atg cct tcg ttg tca gtc tgt gaa ctg gta gaa ggt gag gcc aat       249
Val Met Pro Ser Leu Ser Val Cys Glu Leu Val Glu Gly Glu Ala Asn
50                  55                  60                  65 gtt gtt ggt tgt gtt cgc tac gtt aaa ggt ata atg cac cca ata gaa       297
Val Val Gly Cys Val Arg Tyr Val Lys Gly Ile Met His Pro Ile Glu
                 70                  75                  80 gag gaa ttt tgg gcc aag gag aag ctg gtg gcg ctg gat aat aag aac       345
Glu Glu Phe Trp Ala Lys Glu Lys Leu Val Ala Leu Asp Asn Lys Asn
             85                  90                  95 atg agc tac agt tat att ttt act gag tgt ttt aca ggg tac gag gat       393
Met Ser Tyr Ser Tyr Ile Phe Thr Glu Cys Phe Thr Gly Tyr Glu Asp
         100                 105                 110 tac acg gct acc atg caa ata gtg gag ggt cct gag cac aag gga agt       441
Tyr Thr Ala Thr Met Gln Ile Val Glu Gly Pro Glu His Lys Gly Ser
     115                 120                 125 aga ttt gac tgg tct ttt cag tgc aag tat atc gag ggt atg act gaa       489
Arg Phe Asp Trp Ser Phe Gln Cys Lys Tyr Ile Glu Gly Met Thr Glu
130                 135                 140                 145 tct gca ttc acc gag att ctg cag cat tgg gct act gag ata ggt cag       537
Ser Ala Phe Thr Glu Ile Leu Gln His Trp Ala Thr Glu Ile Gly Gln
                 150                 155                 160 aaa atc gaa gag gtt tgc agt gct tgatcatgaa tatcggtttt cagtgctgtg      591
Lys Ile Glu Glu Val Cys Ser Ala
             165 atgcattatg tgtctttta accttgtctt gtgatataat aaagtaacgt aatatgtgca      651 tgtaataagt aagactgagt gttgtgtgtt caataaaaaa gaatttgctt tttgcaagtt     711 ctagtgcttt tcaaaaaaaa aaaaaaaa                                        739
```

<210> SEQ ID NO 8
<211> LENGTH: 169
<212> TYPE: PRT
<213> ORGANISM: Allium cepa L.

<400> SEQUENCE: 8

```
Met Glu Leu Asn Pro Gly Ala Pro Ala Val Val Ala Asp Ser Ala Asn
1               5                   10                  15

Gly Ala Arg Lys Trp Ser Gly Lys Val His Ala Leu Leu Pro Asn Thr
             20                  25                  30

Lys Pro Glu Gln Ala Trp Thr Leu Leu Lys Asp Phe Ile Asn Leu His
         35                  40                  45

Lys Val Met Pro Ser Leu Ser Val Cys Glu Leu Val Glu Gly Glu Ala
     50                  55                  60

Asn Val Val Gly Cys Val Arg Tyr Val Lys Gly Ile Met His Pro Ile
```

```
                65                  70                  75                  80
Glu Glu Glu Phe Trp Ala Lys Glu Lys Leu Val Ala Leu Asp Asn Lys
                        85                  90                  95

Asn Met Ser Tyr Ser Tyr Ile Phe Thr Glu Cys Phe Thr Gly Tyr Glu
            100                 105                 110

Asp Tyr Thr Ala Thr Met Gln Ile Val Glu Gly Pro Glu His Lys Gly
        115                 120                 125

Ser Arg Phe Asp Trp Ser Phe Gln Cys Lys Tyr Ile Glu Gly Met Thr
    130                 135                 140

Glu Ser Ala Phe Thr Glu Ile Leu Gln His Trp Ala Thr Glu Ile Gly
145                 150                 155                 160

Gln Lys Ile Glu Glu Val Cys Ser Ala
                165
```

<210> SEQ ID NO 9
<211> LENGTH: 648
<212> TYPE: DNA
<213> ORGANISM: Allium ampeloprasum L.
<220> FEATURE:
<221> NAME/KEY: CDS
<222> LOCATION: (1)..(492)
<223> OTHER INFORMATION: P
<220> FEATURE:
<221> NAME/KEY: polyA_site
<222> LOCATION: (632)..(648)
<223> OTHER INFORMATION: P

<400> SEQUENCE: 9

```
atg gcg caa aat cct ggt gtg cct gct gta gcc act gag cca aaa tgg        48
Met Ala Gln Asn Pro Gly Val Pro Ala Val Ala Thr Glu Pro Lys Trp
1               5                   10                  15 aca ggc aag gtc agt gca tcg ctt cca aat aca aag gca gag caa gca        96
Thr Gly Lys Val Ser Ala Ser Leu Pro Asn Thr Lys Ala Glu Gln Ala
                20                  25                  30 tgg aca cta cta aaa gac ttt gtt aac ctt gac aag gtt atg cct tcg       144
Trp Thr Leu Leu Lys Asp Phe Val Asn Leu Asp Lys Val Met Pro Ser
            35                  40                  45 ttg tcg gtt tgt gaa ctg gta gaa ggt aaa ccc aat gct gtt ggt tgt       192
Leu Ser Val Cys Glu Leu Val Glu Gly Lys Pro Asn Ala Val Gly Cys
        50                  55                  60 act cgc tac gtt aaa ggt atg atg cac cca atg gaa gtg gaa ttt tgg       240
Thr Arg Tyr Val Lys Gly Met Met His Pro Met Glu Val Glu Phe Trp
65                  70                  75                  80 gcc aac gag cag ctg gtg gag ctg gat gac gag acc atg acc tac agt       288
Ala Asn Glu Gln Leu Val Glu Leu Asp Asp Glu Thr Met Thr Tyr Ser
                85                  90                  95 tat att ttt act aag gcc ttt aca ggg tat gag ggt tac atg ggt acc       336
Tyr Ile Phe Thr Lys Ala Phe Thr Gly Tyr Glu Gly Tyr Met Gly Thr
            100                 105                 110 atg caa ctt gtg gag gaa agc gat cag aag gga act aga ttt gac tgg       384
Met Gln Leu Val Glu Glu Ser Asp Gln Lys Gly Thr Arg Phe Asp Trp
        115                 120                 125 tct ttt cag tgc aag tac att gag ggt gtg act gcc act tca ttc gct       432
Ser Phe Gln Cys Lys Tyr Ile Glu Gly Val Thr Ala Thr Ser Phe Ala
    130                 135                 140 gct gtt ctg cag att tgg gca gat gag att gcc cag aaa att gaa gag       480
Ala Val Leu Gln Ile Trp Ala Asp Glu Ile Ala Gln Lys Ile Glu Glu
145                 150                 155                 160 att tgc aaa gca tgatcatgaa tatgggtcaa tttgtgatgc tgtgtgcatg           532
Ile Cys Lys Ala
```

```
tgtgttttcc ttctgtcttg tgatgtaatg aaagtaacgt aattccagat gcatgtaatc      592
tgtagtgctt gtgttttcaa taaataagaa tttgctttca aaaaaaaaaa aaaaaa         648

<210> SEQ ID NO 10
<211> LENGTH: 164
<212> TYPE: PRT
<213> ORGANISM: Allium ampeloprasum L.

<400> SEQUENCE: 10

Met Ala Gln Asn Pro Gly Val Pro Ala Val Ala Thr Glu Pro Lys Trp
1               5                   10                  15

Thr Gly Lys Val Ser Ala Ser Leu Pro Asn Thr Lys Ala Glu Gln Ala
            20                  25                  30

Trp Thr Leu Leu Lys Asp Phe Val Asn Leu Asp Lys Val Met Pro Ser
        35                  40                  45

Leu Ser Val Cys Glu Leu Val Glu Gly Lys Pro Asn Ala Val Gly Cys
    50                  55                  60

Thr Arg Tyr Val Lys Gly Met Met His Pro Met Glu Val Glu Phe Trp
65                  70                  75                  80

Ala Asn Glu Gln Leu Val Glu Leu Asp Asp Thr Met Thr Tyr Ser
                85                  90                  95

Tyr Ile Phe Thr Lys Ala Phe Thr Gly Tyr Glu Gly Tyr Met Gly Thr
            100                 105                 110

Met Gln Leu Val Glu Glu Ser Asp Gln Lys Gly Thr Arg Phe Asp Trp
        115                 120                 125

Ser Phe Gln Cys Lys Tyr Ile Glu Gly Val Thr Ala Thr Ser Phe Ala
    130                 135                 140

Ala Val Leu Gln Ile Trp Ala Asp Glu Ile Ala Gln Lys Ile Glu Glu
145                 150                 155                 160

Ile Cys Lys Ala

<210> SEQ ID NO 11
<211> LENGTH: 737
<212> TYPE: DNA
<213> ORGANISM: Allium cepa L.
<220> FEATURE:
<221> NAME/KEY: CDS
<222> LOCATION: (53)..(559)
<223> OTHER INFORMATION: P
<220> FEATURE:
<221> NAME/KEY: polyA_site
<222> LOCATION: (722)..(737)
<223> OTHER INFORMATION: P

<400> SEQUENCE: 11
acaattcaga ctcacattac gttatatcaa gaagattgtc caatcagaaa aa atg gag    58
                                                         Met Glu
                                                           1 cta aat cct ggt gca cct gct gta gtc gct gat agt gct aac gga gct    106
Leu Asn Pro Gly Ala Pro Ala Val Val Ala Asp Ser Ala Asn Gly Ala
        5                   10                  15 cga aaa tgg agc ggc aaa gtc cat gct ttg ctt cca aat aca aag cca    154
Arg Lys Trp Ser Gly Lys Val His Ala Leu Leu Pro Asn Thr Lys Pro
    20                  25                  30 gag caa gca tgg aca cta cta aaa gac ttt att aac ctt cac aag gtc    202
Glu Gln Ala Trp Thr Leu Leu Lys Asp Phe Ile Asn Leu His Lys Val
35                  40                  45                  50 atg cct tcg ttg tca gtc tgt gaa ctg gta gaa ggt gag gcc aat gtt    250
Met Pro Ser Leu Ser Val Cys Glu Leu Val Glu Gly Glu Ala Asn Val
            55                  60                  65
```

```
gtt ggt tgt gtt cgc tac gtt aaa ggt ata atg cac cca ata gaa gag    298
Val Gly Cys Val Arg Tyr Val Lys Gly Ile Met His Pro Ile Glu Glu
         70                  75                  80 gaa ttt tgg gcc aag gag aag ctg gtg gcg ctg gat aat aag aac atg    346
Glu Phe Trp Ala Lys Glu Lys Leu Val Ala Leu Asp Asn Lys Asn Met
         85                  90                  95 agc tac agt tat att ttt act gag tgt ttt aca ggg tac gag gat tac    394
Ser Tyr Ser Tyr Ile Phe Thr Glu Cys Phe Thr Gly Tyr Glu Asp Tyr
        100                 105                 110 acg gct acc atg caa ata gtg gag ggt cct gag cac aag gga agt aga    442
Thr Ala Thr Met Gln Ile Val Glu Gly Pro Glu His Lys Gly Ser Arg
115                 120                 125                 130 ttt gac tgg tct ttt cag tgc aag tat atc gag ggt atg act gaa tct    490
Phe Asp Trp Ser Phe Gln Cys Lys Tyr Ile Glu Gly Met Thr Glu Ser
                135                 140                 145 gca ttc acc gag att ctg cag cat tgg gct act gag ata ggt cag aaa    538
Ala Phe Thr Glu Ile Leu Gln His Trp Ala Thr Glu Ile Gly Gln Lys
            150                 155                 160 atc gaa gag gtt tgc agt gct tgatcatgaa atcggtttt cagtgctgtg        589
Ile Glu Glu Val Cys Ser Ala
            165 atgcattatg tgtctttaa accttgtctt gtgatataat aaagtaacgt aatatgtgca   649 tgtaataagt aagactgagt gttgtgtgtt caataaaaaa gaatttgctt tttgcaagtt  709 ctagtgcttt tcaaaaaaaa aaaaaaaa                                     737

<210> SEQ ID NO 12
<211> LENGTH: 169
<212> TYPE: PRT
<213> ORGANISM: Allium cepa L.

<400> SEQUENCE: 12

Met Glu Leu Asn Pro Gly Ala Pro Ala Val Val Ala Asp Ser Ala Asn
1               5                   10                  15

Gly Ala Arg Lys Trp Ser Gly Lys Val His Ala Leu Leu Pro Asn Thr
            20                  25                  30

Lys Pro Glu Gln Ala Trp Thr Leu Leu Lys Asp Phe Ile Asn Leu His
        35                  40                  45

Lys Val Met Pro Ser Leu Ser Val Cys Glu Leu Val Gly Glu Ala
    50                  55                  60

Asn Val Val Gly Cys Val Arg Tyr Val Lys Gly Ile Met His Pro Ile
65                  70                  75                  80

Glu Glu Glu Phe Trp Ala Lys Glu Lys Leu Val Ala Leu Asp Asn Lys
                85                  90                  95

Asn Met Ser Tyr Ser Tyr Ile Phe Thr Glu Cys Phe Thr Gly Tyr Glu
            100                 105                 110

Asp Tyr Thr Ala Thr Met Gln Ile Val Glu Gly Pro Glu His Lys Gly
        115                 120                 125

Ser Arg Phe Asp Trp Ser Phe Gln Cys Lys Tyr Ile Glu Gly Met Thr
    130                 135                 140

Glu Ser Ala Phe Thr Glu Ile Leu Gln His Trp Ala Thr Glu Ile Gly
145                 150                 155                 160

Gln Lys Ile Glu Glu Val Cys Ser Ala
                165

<210> SEQ ID NO 13
<211> LENGTH: 661
```

```
<212> TYPE: DNA
<213> ORGANISM: Allium ampeloprasum L.
<220> FEATURE:
<221> NAME/KEY: CDS
<222> LOCATION: (1)..(492)
<223> OTHER INFORMATION: P
<220> FEATURE:
<221> NAME/KEY: polyA_site
<222> LOCATION: (637)..(661)
<223> OTHER INFORMATION: P

<400> SEQUENCE: 13 atg gcg caa aat cct ggt gtg cct gct gtt gcc act gag cca aaa tgg      48
Met Ala Gln Asn Pro Gly Val Pro Ala Val Ala Thr Glu Pro Lys Trp
1               5                   10                  15 aca ggc aag gtc agt gca tcg ctt cca aat aca aag cca gag caa gca      96
Thr Gly Lys Val Ser Ala Ser Leu Pro Asn Thr Lys Pro Glu Gln Ala
            20                  25                  30 tgg aca ctg cta aaa gac ttt gtt aac ctt gac aag gtt atg cct tca     144
Trp Thr Leu Leu Lys Asp Phe Val Asn Leu Asp Lys Val Met Pro Ser
        35                  40                  45 ttg tca gtt tgt gaa ctt gta gaa ggt gaa ccc aat gcc gtt ggt tgt     192
Leu Ser Val Cys Glu Leu Val Glu Gly Glu Pro Asn Ala Val Gly Cys
50                  55                  60 act cgc tac gtt aaa ggt atg atg cac cca atg gaa gtg gaa ttt tgg     240
Thr Arg Tyr Val Lys Gly Met Met His Pro Met Glu Val Glu Phe Trp
65                  70                  75                  80 gcc aac gag cag ctg gtg gag ctg gat gac gag acc atg acc tac agt     288
Ala Asn Glu Gln Leu Val Glu Leu Asp Asp Glu Thr Met Thr Tyr Ser
                85                  90                  95 tat att ttt act aag gcc ttt aca ggg tat gag ggt tac atg ggt acc     336
Tyr Ile Phe Thr Lys Ala Phe Thr Gly Tyr Glu Gly Tyr Met Gly Thr
            100                 105                 110 atg caa ctt gtg gag gaa agc gat cag aag gga act agg ttt gac tgg     384
Met Gln Leu Val Glu Glu Ser Asp Gln Lys Gly Thr Arg Phe Asp Trp
        115                 120                 125 tct ttt cag tgc aag tac att gag ggt gtg act gcc aca tca ttc gct     432
Ser Phe Gln Cys Lys Tyr Ile Glu Gly Val Thr Ala Thr Ser Phe Ala
130                 135                 140 gct gtt ctg cag att tgg gca gat gag att gcc cag aaa att gaa gag     480
Ala Val Leu Gln Ile Trp Ala Asp Glu Ile Ala Gln Lys Ile Glu Glu
145                 150                 155                 160 att tgc aaa gca tgatcatgaa tatgggtcaa tttgtgatgc tgtgtgcatg         532
Ile Cys Lys Ala tgtgttttcc attctgtctt gtgatgtaat gaagtaacgt aattaccaga tgcatgtaat   592
ctgtagtggc tgtgttttca ataaataaga atttgctttc ttgcaaaaaa aaaaaaaaa   652 aaaaaaaaa                                                           661

<210> SEQ ID NO 14
<211> LENGTH: 164
<212> TYPE: PRT
<213> ORGANISM: Allium ampeloprasum L.

<400> SEQUENCE: 14

Met Ala Gln Asn Pro Gly Val Pro Ala Val Ala Thr Glu Pro Lys Trp
1               5                   10                  15

Thr Gly Lys Val Ser Ala Ser Leu Pro Asn Thr Lys Pro Glu Gln Ala
            20                  25                  30

Trp Thr Leu Leu Lys Asp Phe Val Asn Leu Asp Lys Val Met Pro Ser
        35                  40                  45
```

```
Leu Ser Val Cys Glu Leu Val Glu Gly Glu Pro Asn Ala Val Gly Cys
 50                  55                  60

Thr Arg Tyr Val Lys Gly Met Met His Pro Met Glu Val Glu Phe Trp
 65                  70                  75                  80

Ala Asn Glu Gln Leu Val Glu Leu Asp Asp Glu Thr Met Thr Tyr Ser
                 85                  90                  95

Tyr Ile Phe Thr Lys Ala Phe Thr Gly Tyr Glu Gly Tyr Met Gly Thr
            100                 105                 110

Met Gln Leu Val Glu Glu Ser Asp Gln Lys Gly Thr Arg Phe Asp Trp
        115                 120                 125

Ser Phe Gln Cys Lys Tyr Ile Glu Gly Val Thr Ala Thr Ser Phe Ala
130                 135                 140

Ala Val Leu Gln Ile Trp Ala Asp Glu Ile Ala Gln Lys Ile Glu Glu
145                 150                 155                 160

Ile Cys Lys Ala

<210> SEQ ID NO 15
<211> LENGTH: 726
<212> TYPE: DNA
<213> ORGANISM: Allium ampeloprasum L.
<220> FEATURE:
<221> NAME/KEY: CDS
<222> LOCATION: (57)..(563)
<223> OTHER INFORMATION: P
<220> FEATURE:
<221> NAME/KEY: polyA_site
<222> LOCATION: (717)..(726)
<223> OTHER INFORMATION: P

<400> SEQUENCE: 15
acacacaact cagacccaca tttcgttgta tttagtagat tattcagtca ggaaaa atg      59
                                                            Met
                                                             1 atg aca tat cct gga aat cgt gct gta gcc act gat ggt gcc aaa gaa      107
Met Thr Tyr Pro Gly Asn Arg Ala Val Ala Thr Asp Gly Ala Lys Glu
         5                  10                  15 gct cca aaa tgg aaa ggc aaa gcc tat gcc ttg ctt cca aat aca aag      155
Ala Pro Lys Trp Lys Gly Lys Ala Tyr Ala Leu Leu Pro Asn Thr Lys
     20                  25                  30 cca gag cac gcg tgg aaa cta cta aaa gac ttc att aac ctt cac aag      203
Pro Glu His Ala Trp Lys Leu Leu Lys Asp Phe Ile Asn Leu His Lys
 35                  40                  45 acc atg cca tcg ctg tca gtt tgt gaa ctg gta gaa ggt gag gtc aat      251
Thr Met Pro Ser Leu Ser Val Cys Glu Leu Val Glu Gly Glu Val Asn
 50                  55                  60                  65 gct gta ggt tgt gtt cgt cat gtt aaa ggt ata atg cat cca atg gag      299
Ala Val Gly Cys Val Arg His Val Lys Gly Ile Met His Pro Met Glu
                 70                  75                  80 cag gag ttt tgg gct aag gag aag ctg gtg gca gtc gat gac aag gcc      347
Gln Glu Phe Trp Ala Lys Glu Lys Leu Val Ala Val Asp Asp Lys Ala
             85                  90                  95 atg agc tac agt tat att ttt act gag tgt ttt aca ggg tac gag gat      395
Met Ser Tyr Ser Tyr Ile Phe Thr Glu Cys Phe Thr Gly Tyr Glu Asp
        100                 105                 110 tac acg gcc acc atg caa att atg gat gga tgc gag cat aag gga agc      443
Tyr Thr Ala Thr Met Gln Ile Met Asp Gly Cys Glu His Lys Gly Ser
    115                 120                 125 aga ttt gag tgg tcc ttc cag tgt aac tac atc gag ggt atg act gaa      491
Arg Phe Glu Trp Ser Phe Gln Cys Asn Tyr Ile Glu Gly Met Thr Glu
130                 135                 140                 145
```

```
tct gcc ttc act gac att ctg cag cat tgg acc act gag att ggt cag      539
Ser Ala Phe Thr Asp Ile Leu Gln His Trp Thr Thr Glu Ile Gly Gln
                150                 155                 160 aaa att gaa gag att tgc agt gct tgattatgaa tatcggttta tgctgtgatg     593
Lys Ile Glu Glu Ile Cys Ser Ala
                165 caatgtgtgt gtattaatcc ctgccttgtg atgtgataaa ataacttaat atgtcatatg    653 catgtaatag gcaagccagg gtggtgttgt gttctcaata aaaagcattt gcttttgca     713 taaaaaaaaa aaa                                                        726
```

```
<210> SEQ ID NO 16
<211> LENGTH: 169
<212> TYPE: PRT
<213> ORGANISM: Allium ampeloprasum L.

<400> SEQUENCE: 16
```

```
Met Met Thr Tyr Pro Gly Asn Arg Ala Val Ala Thr Asp Gly Ala Lys
1               5                   10                  15

Glu Ala Pro Lys Trp Lys Gly Lys Ala Tyr Ala Leu Leu Pro Asn Thr
                20                  25                  30

Lys Pro Glu His Ala Trp Lys Leu Leu Lys Asp Phe Ile Asn Leu His
            35                  40                  45

Lys Thr Met Pro Ser Leu Ser Val Cys Glu Leu Val Glu Gly Glu Val
        50                  55                  60

Asn Ala Val Gly Cys Val Arg His Val Lys Gly Ile Met His Pro Met
65                  70                  75                  80

Glu Gln Glu Phe Trp Ala Lys Glu Lys Leu Val Ala Val Asp Asp Lys
                85                  90                  95

Ala Met Ser Tyr Ser Tyr Ile Phe Thr Glu Cys Phe Thr Gly Tyr Glu
                100                 105                 110

Asp Tyr Thr Ala Thr Met Gln Ile Met Asp Gly Cys Glu His Lys Gly
            115                 120                 125

Ser Arg Phe Glu Trp Ser Phe Gln Cys Asn Tyr Ile Glu Gly Met Thr
        130                 135                 140

Glu Ser Ala Phe Thr Asp Ile Leu Gln His Trp Thr Thr Glu Ile Gly
145                 150                 155                 160

Gln Lys Ile Glu Glu Ile Cys Ser Ala
                165
```

```
<210> SEQ ID NO 17
<211> LENGTH: 25
<212> TYPE: DNA
<213> ORGANISM: Artificial
<220> FEATURE:
<223> OTHER INFORMATION: PCR primer

<400> SEQUENCE: 17
aattaaggga gtcacgttat gaccc                                           25

<210> SEQ ID NO 18
<211> LENGTH: 23
<212> TYPE: DNA
<213> ORGANISM: Artificial
<220> FEATURE:
<223> OTHER INFORMATION: PCR primer

<400> SEQUENCE: 18
agaaacttct cgacagacgt cgc                                             23
```

```
<210> SEQ ID NO 19
<211> LENGTH: 23
<212> TYPE: DNA
<213> ORGANISM: Artificial
<220> FEATURE:
<223> OTHER INFORMATION: PCR primer

<400> SEQUENCE: 19
gtggcaatcc ctttcacaac ctg                                              23

<210> SEQ ID NO 20
<211> LENGTH: 20
<212> TYPE: DNA
<213> ORGANISM: Artificial
<220> FEATURE:
<223> OTHER INFORMATION: PCR primer

<400> SEQUENCE: 20
tggagggtcc tgagcacaag                                                  20

<210> SEQ ID NO 21
<211> LENGTH: 27
<212> TYPE: DNA
<213> ORGANISM: Artificial
<220> FEATURE:
<223> OTHER INFORMATION: PCR primer

<400> SEQUENCE: 21
tgcgggactc taatcataaa aacccat                                          27
```